US005892014A

United States Patent [19]
Coughlin et al.

[11] Patent Number: 5,892,014
[45] Date of Patent: Apr. 6, 1999

[54] DNA ENCODING A PROTEASE-ACTIVATED RECEPTOR 3

[75] Inventors: Shaun R. Coughlin, Tiburon; Hiroaki Ishihara; Andrew Connolly, both of San Francisco, all of Calif.

[73] Assignee: The Regents of the University of California, Oakland, Calif.

[21] Appl. No.: 742,440

[22] Filed: Oct. 30, 1996

[51] Int. Cl.$^6$ .......................... C12N 15/12; C12N 15/63; C12N 5/10

[52] U.S. Cl. .................. 536/23.5; 435/69.1; 435/325; 435/320.1

[58] Field of Search .................. 536/23.5; 435/69.1, 435/325, 320.1; 530/350, 327

[56] References Cited

U.S. PATENT DOCUMENTS 5,256,766  10/1993  Coughlin ................................ 530/327
5,686,597  11/1997  Coleman et al. ....................... 536/23.5

FOREIGN PATENT DOCUMENTS

WO 95/19436   7/1995   WIPO .

OTHER PUBLICATIONS

Amatrude III, T.T., et al. (1991) "Gα16, a G protein αsubunit specifically expressed in hematopoietic cells," *Proc. Natl. Acad. Sci.* 88:5587–91.

Connolly, A., et al. (1996) "Role of the thrombin receptor in development and evidence for a second receptor," *Nature* 381:516–519.

Ishii, K., et al. (1993) "Kinetics of thrombin receptor cleavage on intact cells," *J. Biol. Chem.* 268:9780–9786.

Ishii, K., et al. (1995) "Determinants of thrombin receptor cleavage," *J. Biol. Chem.* 270:16435–16440.

Julius, D., et al. (1988) "Molecular characterization of a functional cDNA encoding the serotonin 1c receptor" *Science* 241:558–564.

Liu, L., et al. (1991) "The region of the thrombin receptor resembling hirudin binds to thrombin and alters enzyme specificity," *J. Biol. Chem.* 266:16977–16980.

Mathews, I.I., et al. (1994) "Crystallographic structures of thrombin complexed with thrombin receptor peptides: Existence of expected and novel binding modes," *Biochem.* 33:3266–3279.

Nonevicz, T., et al. (1996) "Thrombin receptor activating mutations," *J. Biol. Chem.* 271:702–706.

Nystedt, S., et al. (1994) "Molecular cloning of a potential proteinase activated receptor," *Proc. Natl. Acad. Sci. USA*, 91:9208–9212.

Scarborough, R.M., et al. (1992) "Tethered ligand agonist peptides," *J. Biol. Chem.* 267:13146–13149.

Soifer, S.J., et al. (1993) "Disparate temporal expression of the prothrombin and thrombin receptor genes during mouse development," *Am. J. Pathol.* 144:60–69.

Vu, T.–K.H., et al. (1991) "Molecular cloning of a functional thrombin receptor reveals a novel protcolytic mechanism of receptor activation," *Cell* 64:1057–1068.

Vu, T.–K.H., et al. (1991) "Domains specifying thrombin––receptor interaction," *Nature* 353:674–677.

*Primary Examiner*—Lila Feisee
*Assistant Examiner*—Michael Pak
*Attorney, Agent, or Firm*—Bozicevic & Reed LLP

[57] ABSTRACT

Disclosed are cDNAs and genomic DNAs encoding protease-activated receptor 3 (PAR3) from mouse and human, and the recombinant polypeptides expressed from such cDNAs. The recombinant receptor polypeptides, receptor fragments and analogs expressed on the surface of cells are used in methods of screening candidate compounds for their ability to act as agonists or antagonists to the effects of interaction between thrombin and PAR3. Agonists are used as therapeutics to treat wounds, thrombosis, atherosclerosis, restenosis, inflammation, and other thrombin-activated disorders. Antagonists are used as therapeutics to control blood coagulation and thereby treating heart attack and stroke. Antagonists mediate inflammatory and proliferative responses to injury as occur in normal wound healing and variety of diseases including atherosclerosis, restenosis, pulmonary inflammation (ARDS) and glomerulosclerosis. Antibodies specific for a protease-activated receptor 3 (or receptor fragment or analog) and their use as a therapeutic are also disclosed.

4 Claims, 16 Drawing Sheets

FIG. 1-1

```
                10            20            30            40            50
                 *             *             *             *             *
          TG ACT TTG TAT ACT TAA CAA CAT CCT GTA GCC GGG TCT CAG GAC ATC AAG
          AC TGA AAC ATA TGA ATT GTT GTA GGA CAT CGG CCC AGA GTC CTG TAG TTC
             T   L   Y   T   *   Q   H   P   V   A   G   S   Q   D   I   K>
                      60            70            80            90
                       *   *   *    *    *    *    *    *    *
          ATG AAA ATC CTT ATC TTG GTT GCA GCT GGG CTG CTG TTT CTG CCA GTC
          TAC TTT TAG GAA TAG AAC CAA CGT CGA CCC GAC GAC AAA GAC GGT CAG
           M   K   I   L   I   L   V   A   A   G   L   L   F   L   P   V>
         100           110           120           130           140
           *    *   *    *    *   *    *    *   *    *    *   *    *   *
         ACT GTT TGC CAA AGT GGC ATA AAT GTT TCA GAC AAC TCA GCA AAG CCA
         TGA CAA ACG GTT TCA CCG TAT TTA CAA AGT CTG TTG AGT CGT TTC GGT
          T   V   C   Q   S   G   I   N   V   S   D   N   S   A   K   P>
              150           160           170           180           190
                *     *     *     *     *     *     *     *     *
         ACC TTA ACT ATT AAG AGT TTT AAT GGG GGT CCC CAA AAT ACC TTT GAA
         TGG AAT TGA TAA TTC TCA AAA TTA CCC CCA GGG GTT TTA TGG AAA CTT
          T   L   T   I   K   S   F   N   G   G   P   Q   N   T   F   E>
              200           210           220           230           240
               *    *    *    *    *    *    *    *    *    *
         GAA TTC CCA CTT TCT GAC ATA GAG GGC TGG ACA GGA GCC ACC ACA ACT
         CTT AAG GGT GAA AGA CTG TAT CTC CCG ACC TGT CCT CGG TGG TGT TGA
          E   F   P   L   S   D   I   E   G   W   T   G   A   T   T   T>
                  250           260           270           280           290
                   *    *    *    *    *    *    *    *    *    *
         ATA AAA GCG GAG TGT CCC GAG GAC AGT ATT TCA ACT CTC CAC GTG AAT
         TAT TTT CGC CTC ACA GGG CTC CTG TCA TAA AGT TGA GAG GTG CAC TTA
          I   K   A   E   C   P   E   D   S   I   S   T   L   H   V   N>
                    300           310           320           330
                     *     *     *     *     *     *     *     *     *
         AAT GCT ACC ATA GGA TAC CTG AGA AGT TCC TTA AGT ACC CAA GTG ATA
         TTA CGA TGG TAT CCT ATG GAC TCT TCA AGG AAT TCA TGG GTT CAC TAT
          N   A   T   I   G   Y   L   R   S   S   L   S   T   Q   V   I>
         340           350           360           370           380
           *   *    *    *    *    *    *    *    *    *
         CCT GCC ATC TAT ATC CTG CTG TTT GTG GTT GGT GTA CCA TCC AAC ATC
         GGA CGG TAG ATA TAG GAC GAC AAA CAC CAA CCA CAT GGT AGG TTG TAG
          P   A   I   Y   I   L   L   F   V   V   G   V   P   S   N   I>
              390           400           410           420           430
                *     *     *     *     *     *     *     *     *
         GTG ACC CTG TGG AAA CTC TCC TTA AGG ACC AAA TCC ATC AGT CTG GTC
         CAC TGG GAC ACC TTT GAG AGG AAT TCC TGG TTT AGG TAG TCA GAC CAG
          V   T   L   W   K   L   S   L   R   T   K   S   I   S   L   V>
```

FIG. 1-2

```
          440         450         460         470         480
       *    *    *    *    *    *    *    *    *    *
       ATC TTT CAC ACC AAC CTG GCC ATC GCA GAT CTC CTT TTC TGT GTC ACA
       TAG AAA GTG TGG TTG GAC CGG TAG CGT CTA GAG GAA AAG ACA CAG TGT
        I   F   H   T   M   L   A   I   A   D   L   L   F   C   V   T>
          490         500         510         520         530
       *    *    *    *    *    *    *    *    *    *
       CTG CCA TTT AAG ATC GCC TAC CAT CTC AAT GGC AAC AAC TGG GTA TTT
       GAC GGT AAA TTC TAG CGG ATG GTA GAG TTA CCG TTG TTG ACC CAT AAA
        L   P   F   K   I   A   Y   H   L   N   G   N   N   W   V   F>
              540         550         560         570
          *    *    *    *    *    *    *    *    *
       GGC GAG GTC ATG TGC CGG ATC ACC ACG GTC GTT TTC TAC GGC AAC ATG
       CCG CTC CAG TAC ACG GCC TAG TGG TGC CAG CAA AAG ATG CCG TTG TAC
        G   E   V   M   C   R   I   T   T   V   V   F   Y   G   N   M>
 580         590         600         610         620
    *    *    *    *    *    *    *    *    *    *
    TAC TGC GCT ATC CTG ATC CTC ACT TGC ATG GGC ATC AAC CGC TAC CTG
    ATG ACG CGA TAG GAC TAG GAG TGA ACG TAC CCG TAG TTG GCG ATG GAC
     Y   C   A   I   L   I   L   T   C   M   G   I   N   R   Y   L>
          630         640         650         660         670
       *    *    *    *    *    *    *    *    *
       GCC ACG GCT CAC CCT TTC ACA TAC CAG AAG CTG CCC AAA CGC AGC TTC
       CGG TGC CGA GTG GGA AAG TGT ATG GTC TTC GAC GGG TTT GCG TCG AAG
        A   T   A   H   P   F   T   Y   Q   K   L   P   K   R   S   F>
          680         690         700         710         720
       *    *    *    *    *    *    *    *    *    *
       TCC TTG CTC ATG TGT GGC ATA GTG TGG GTC ATG GTT TTC TTA TAC ATG
       AGG AAC GAG TAC ACA CCG TAT CAC ACC CAG TAC CAA AAG AAT ATG TAC
        S   L   L   M   C   G   I   V   W   V   M   V   F   L   Y   M>
              730         740         750         760         770
          *    *    *    *    *    *    *    *    *    *
          CTG CCC TTT GTC ATC CTG AAG CAG GAG TAC CAC CTC GTC CAC TCA GAG
          GAC GGG AAA CAG TAG GAC TTC GTC CTC ATG GTG GAG CAG GTG AGT CTC
           L   P   F   V   I   L   K   Q   E   Y   H   L   V   H   S   E>
                  780         790         800         810
              *    *    *    *    *    *    *    *    *
              ATC ACC ACC TGC CAC GAT GTC GTC GAC GCG TGC GAG TCC CCA TCA TCC
              TAG TGG TGG ACG GTG CTA CAG CAG CTG CGC ACG CTC AGG GGT AGT AGG
               I   T   T   C   H   D   V   V   D   A   C   E   S   P   S   S>
 820         830         840         850         860
    *    *    *    *    *    *    *    *    *    *
    TTC CGA TTC TAC TAC TTC GTC TCC TTA GCA TTC TTT GGG TTC CTC ATC
    AAG GCT AAG ATG ATG AAG CAG AGG AAT CGT AAG AAA CCC AAG GAG TAG
     F   R   F   Y   Y   F   V   S   L   A   F   F   G   F   L   I>
```

FIG. 1-3

```
       870         880         890         900         910
        *     *     *     *     *     *     *     *     *
CCG TTT GTG ATC ATC ATC TTC TGT TAC ACG ACT CTC ATC CAC AAA CTT
GGC AAA CAC TAG TAG TAG AAG ACA ATG TGC TGA GAG TAG GTG TTT GAA
 P   F   V   I   I   I   F   C   Y   T   T   L   I   H   K   L>
          920         930         940         950         960
     *     *     *     *     *     *     *     *     *     *
AAA TCA AAG GAT CGG ATA TGG CTG GGC TAC ATC AAG GCC GTC CTC CTC
TTT AGT TTC CTA GCC TAT ACC GAC CCG ATG TAG TTC CGG CAG GAG GAG
 K   S   K   D   R   I   W   L   G   Y   I   K   A   V   L   L>
       970         980         990        1000        1010
  *     *     *     *     *     *     *     *     *     *
ATC CTT GTG ATT TTC ACA ATT TGC TTT GCC CCC ACC AAC ATC ATA CTC
TAG GAA CAC TAA AAG TGT TAA ACG AAA CGG GGG TGG TTG TAG TAT GAG
 I   L   V   I   F   T   I   C   F   A   P   T   N   I   I   L>
         1020        1030        1040        1050
     *     *     *     *     *     *     *     *     *
GTA ATC CAC CAT GCC AAC TAC TAC TAC CAC AAT ACC GAC AGC TTG TAC
CAT TAG GTG GTA CGG TTG ATG ATG ATG GTG TTA TGG CTG TCG AAC ATG
 V   I   H   H   A   N   Y   Y   Y   H   N   T   D   S   L   Y>
1060        1070        1080        1090        1100
  *     *     *     *     *     *     *     *     *     *
TTT ATG TAT CTT ATT GCT CTG TGC CTG GGG AGC CTG AAT AGC TGC CTA
AAA TAC ATA GAA TAA CGA GAC ACG GAC CCC TCG GAC TTA TCG ACG GAT
 F   M   Y   L   I   A   L   C   L   G   S   L   N   S   C   L>
  1100        1120        1130        1140        1150
     *     *     *     *     *     *     *     *     *
GAT CCA TTC CTT TAC TTT GTC ATG TCG AAA GTT GTA GAT CAG CTT AAT
CTA GGT AAG GAA ATG AAA CAG TAC AGC TTT CAA CAT CTA GTC GAA TTA
 D   P   F   L   Y   F   V   M   S   K   V   V   D   Q   L   N>
       1160        1170        1180        1190        1200
  *     *     *     *     *     *     *     *     *     *
CCT TAG TCG GCA ATG GCA AGA CCA CTT TAG AGA CCA AGG AGA GAT ATC
GGA ATC AGC CGT TAC CGT TCT GGT GAA ATC TCT GGT TCC TCT CTA TAG
 P   *   S   A   M   A   R   P   L   *   R   P   R   R   D   I>
          1210        1220
     *     *     *     *
TGG GAA GAC ATA CAT GCT TGG C
ACC CTT CTG TAT GTA CGA ACC G
 W   E   D   I   H   A   W   X>
```

FIG. 2-1

```
          10         20         30         40         50
           *          *          *          *          *
     CCATATGCTA ATATTTCCTT TCAATTACAG GCATAAATGT TTCAGACAAC 60         70         80         90        100
           *          *          *          *          *
     TCAGCAAAGC CAACCTTAAC TATTAAGAGT TTTAATGGGG GTCCCCAAAA 110        120        130        140        150
           *          *          *          *          *
     TACCTTTGAA GAATTC---- ---TACAACT CTCCATGTGA ATAATGCTAC 160        170        180        190        200
           *          *          *          *          *
     CATGGGATAC CTGAGAAGTT CCTTAAGTAC CAAAGTGATA CCTGCCATCT 210        220        230        240        250
           *          *          *          *          *
     ACATCCTGGT GTTTGTGATT GGTGTACCAG CGAACATCGT GACCCTGTGG 260        270        280        290        300
           *          *          *          *          *
     AAACTCTCCT CAAGGACCAA ATCCATCTGT CTGGTCATCT TTCACACCAA 310        320        330        340        350
           *          *          *          *          *
     CCTGGCCATC GCGGATCTCC TTTTCTGTGT CACGCTGCCG TTTAAGATC- 360        370        380        390        400
           *          *          *          *          *
     -CCTACCATC TCAATGGCAA CAACTGGGTA TTTGGCGAGG TCATGTGCCG 410        420        430        440        450
           *          *          *          *          *
     GATCACCACG GTCGTTTTCT ACGGCAACAT GTACTGCGCT A---TCCTGA 460        470        480        490        500
           *          *          *          *          *
     TCCTCACCTG CATGGGCATC AACCGCTACC TGGCCACGGC TCACCCTTTC 510        520        530        540        550
           *          *          *          *          *
     ACATACCAGA AGCTGCCCAA ACGCAGCTTC TCCATGCTCA TGTGTGGCAT 560        570        580        590        600
           *          *          *          *          *
     GGTGTGGGTC ATGGTTTTCT TATACATGCT GCCCTTTGTC ATCC---AAG 610        620        630        640        650
           *          *          *          *          *
     CAGGAGTACC ACCTCGTCCA CTCCGAGATC ACCACCTGCC ACGATGTCGT
```

FIG. 2-2

```
             660        670        680        690        700
              *  *       *  *       *  *       *  *       *  *
         CGACGCGTGC GANTCCCCAT CATCCTTCCG ATTCTACTAC TTCGTCTCCT
             710        720        730        740        750
              *  *       *  *       *  *       *  *       *  *
         TAGCATTCTT TGGGTTCCTC ATCCCGTTTG TGATCATCAT CTTCTGTTAC
             760        770        780        790        800
              *  *       *  *       *  *       *  *       *  *
         ACGACTCTCA TCCACAAACT TAAATCAAAA GATCNGATAT GGCTGGGCTA
             810        820        830        840        850
              *  *       *  *       *  *       *  *       *  *
         CATCAAGGCC GTCCTCCTCA TCCTTGTGAA TTTCACCATC TGCTTCCCCC
             860        870        880        890        900
              *  *       *  *       *  *       *  *       *  *
         CCACCAAG-- ----GATATC TGGGAAGACG TACATGCTTG GCTGACTTGT
             910        920        930        940        950
              *  *       *  *       *  *       *  *       *  *
         GCATGGCACC ATCAGCTCAA TTTTTAATTT TTTAATTTTA ATTTAATTTA
             960        970        980        990       1000
              *  *       *  *       *  *       *  *       *  *
         ATTTTATGTT TTTGAGACAG AGCCTCACTG TGTAGTCCTG GCTGGCCTGG
            1010       1020       1030       1040       1050
              *  *       *  *       *  *       *  *       *  *
         CTGGTTCTCT ATTTAGACCA GGTTAGCCTT GAACTCACAG AGATCTGCCT
            1060       1070       1080       1090       1100
              *  *       *  *       *  *       *  *       *  *
         GCTTCTGCCT CCCAAGTGCT GGGTTCAACC AGGTCTGGCA AGCGCTCCAT
            1110       1120
              *  *       *  *
         TTTTCAGCTC CTCTGCAACA GTGC
```

FIG. 3-1

```
              10          20          30          40
         *     *     *     *     *     *     *     *     *
        TGC   TCC   ATG   ATT   TTA   CAG   ATT   TCA   TAA   CGT   TTA   AGA   GAC   GGG   ACT   CAG
        ACG   AGG   TAC   TAA   AAT   GTC   TAA   AGT   ATT   GCA   AAT   TCT   CTG   CCC   TGA   GTC
         C     S     M     I     L     Q     I     S     *     R     L     R     D     G     T     Q>
         50          60          70          80          90
         *     *     *     *     *     *     *     *     *     *
        GTC   ATC   AAA   ATG   AAA   GCC   CTC   ATC   TTT   GCA   GCT   GCT   GGC   CTC   CTG   CTT
        CAG   TAG   TTT   TAC   TTT   CGG   GAG   TAG   AAA   CGT   CGA   CGA   CCG   GAG   GAC   GAA
         V     I     K     M     K     A     L     I     F     A     A     A     G     L     L     L>
              100         110         120         130         140
         *     *     *     *     *     *     *     *     *
        CTG   TTG   CCC   ACT   TTT   TGT   CAG   AGT   GGC   ATG   GAA   AAT   GAT   ACA   AAC   AAC
        GAC   AAC   GGG   TGA   AAA   ACA   GTC   TCA   CCG   TAC   CTT   TTA   CTA   TGT   TTG   TTG
         L     L     P     T     F     C     Q     S     G     M     E     N     D     T     N     N>
              150         160         170         180         190
         *     *     *     *     *     *     *     *     *     *
        TTG   GCA   AAG   CCA   ACC   TTA   CCC   ATT   AAG   ACC   TTT   CGT   GGA   GCT   CCC   CCA
        AAC   CGT   TTC   GGT   TGG   AAT   GGG   TAA   TTC   TGG   AAA   GCA   CCT   CGA   GGG   GGT
         L     A     K     P     T     L     P     I     K     T     F     R     G     A     P     P>
                    200         210         220         230         240
         *     *     *     *     *     *     *     *     *     *
        AAT   TCT   TTT   GAA   GAG   TTC   CCC   TTT   TCT   GCC   TTG   GAA   GGC   TGG   ACA   GGA
        TTA   AGA   AAA   CTT   CTC   AAG   GGG   AAA   AGA   CGG   AAC   CTT   CCG   ACC   TGT   CCT
         N     S     F     E     E     F     P     F     S     A     L     E     G     W     T     G>
                    250         260         270         280
         *     *     *     *     *     *     *     *     *
        GCC   ACG   ATT   ACT   GTA   AAA   ATT   AAG   TGC   CCT   GAA   GAA   AGT   GCT   TCA   CAT
        CGG   TGC   TAA   TGA   CAT   TTT   TAA   TTC   ACG   GGA   CTT   CTT   TCA   CGA   AGT   GTA
         A     T     I     T     V     K     I     K     C     P     E     E     S     A     S     H>
         290         300         310         320         330
         *     *     *     *     *     *     *     *     *     *
        CTC   CAT   GTG   AAA   AAT   GCT   ACC   ATG   GGG   TAC   CTG   ACC   AGC   TCC   TTA   AGT
        GAG   GTA   CAC   TTT   TTA   CGA   TGG   TAC   CCC   ATG   GAC   TGG   TCG   AGG   AAT   TCA
         L     H     V     K     N     A     T     M     G     Y     L     T     S     S     L     S>
              340         350         360         370         380
         *     *     *     *     *     *     *     *     *
        ACT   AAA   CTG   ATA   CCT   GCC   ATC   TAC   CTC   CTG   GTG   TTT   GTA   GTT   GGT   GTC
        TGA   TTT   GAC   TAT   GGA   CGG   TAG   ATG   GAG   GAC   CAC   AAA   CAT   CAA   CCA   CAG
         T     K     L     I     P     A     I     Y     L     L     V     F     V     V     G     V>
              390         400         410         420         430
         *     *     *     *     *     *     *     *     *     *
        CCG   GCC   AAT   GCT   GTG   ACC   CTG   TGG   ATG   CTT   TTC   TTC   AGG   ACC   AGA   TCC
        GGC   CGG   TTA   CGA   CAC   TGG   GAC   ACC   TAC   GAA   AAG   AAG   TCC   TGG   TCT   AGG
         P     A     N     A     V     T     L     W     M     L     F     F     R     T     R     S>
```

FIG. 3-2

```
              440         450         460         470         480
          *    *    *    *    *    *    *    *    *    *
         ATC  TGT  ACC  ACT  GTA  TTC  TAC  ACC  AAC  CTG  GCC  ATT  GCA  GAT  TTT  CTT
         TAG  ACA  TGG  TGA  CAT  AAG  ATG  TGG  TTG  GAC  CGG  TAA  CGT  CTA  AAA  GAA
          I    C    T    T    V    F    Y    T    N    L    A    I    A    D    F    L>
                   490         500         510         520
              *    *    *    *    *    *    *    *    *    *
         TTT  TGT  GTT  ACA  TTG  CCC  TTT  AAG  ATA  GCT  TAT  CAT  CTC  AAT  GGG  AAC
         AAA  ACA  CAA  TGT  AAC  GGG  AAA  TTC  TAT  CGA  ATA  GTA  GAG  TTA  CCC  TTG
          F    C    V    T    L    P    F    K    I    A    Y    H    L    N    G    N>
         530         540         550         560         570
          *    *    *    *    *    *    *    *    *    *
         AAC  TGG  GTA  TTT  GGA  GAG  GTC  CTG  TGC  CGG  GCC  ACC  ACA  GTC  ATC  TTC
         TTG  ACC  CAT  AAA  CCT  CTC  CAG  GAC  ACG  GCC  CGG  TGG  TGT  CAG  TAG  AAG
          N    W    V    F    G    E    V    L    C    R    A    T    T    V    I    F>
             580         590         600         610         620
          *    *    *    *    *    *    *    *    *
         TAT  GGC  AAC  ATG  TAC  TGC  TCC  ATT  CTG  CTC  CTT  GCC  TGC  ATC  AGC  ATC
         ATA  CCG  TTG  TAC  ATG  ACG  AGG  TAA  GAC  GAG  GAA  CGG  ACG  TAG  TCG  TAG
          Y    G    N    M    Y    C    S    I    L    L    L    A    C    I    S    I>
             630         640         650         660         670
          *    *    *    *    *    *    *    *    *    *
         AAC  CGC  TAC  CTG  GCC  ATC  GTC  CAT  CCT  TTC  ACC  TAC  CGG  GGC  CTG  CCC
         TTG  GCG  ATG  GAC  CGG  TAG  CAG  GTA  GGA  AAG  TGG  ATG  GCC  CCG  GAC  GGG
          N    R    Y    L    A    I    V    H    P    F    T    Y    R    G    L    P>
                  680         690         700         710         720
              *    *    *    *    *    *    *    *    *    *
         AAG  CAC  ACC  TAT  GCC  TTG  GTA  ACA  TGT  GGA  CTG  GTG  TGG  GCA  ACA  GTT
         TTC  GTG  TGG  ATA  CGG  AAC  CAT  TGT  ACA  CCT  GAC  CAC  ACC  CGT  TGT  CAA
          K    H    T    Y    A    L    V    T    C    G    L    V    W    A    T    V>
                       730         740         750         760
              *    *    *    *    *    *    *    *    *
         TTC  TTA  TAT  ATG  CTG  CCA  TTT  TTC  ATA  CTG  AAG  CAG  GAA  TAT  TAT  CTT
         AAG  AAT  ATA  TAC  GAC  GGT  AAA  AAG  TAT  GAC  TTC  GTC  CTT  ATA  ATA  GAA
          F    L    Y    M    L    P    F    F    I    L    K    Q    E    Y    Y    L>
         770         780         790         800         810
          *    *    *    *    *    *    *    *    *    *
         GTT  CAG  CCA  GAC  ATC  ACC  ACC  TGC  CAT  GAT  GTT  CAC  AAC  ACT  TGC  GAG
         CAA  GTC  GGT  CTG  TAG  TGG  TGG  ACG  GTA  CTA  CAA  GTG  TTG  TGA  ACG  CTC
          V    Q    P    D    I    T    T    C    H    D    V    H    N    T    C    E>
             820         830         840         850         860
          *    *    *    *    *    *    *    *    *
         TCC  TCA  TCT  CCC  TTC  CAA  CTC  TAT  TAC  TTC  ATC  TCC  TTG  GCA  TTC  TTT
         AGG  AGT  AGA  GGG  AAG  GTT  GAG  ATA  ATG  AAG  TAG  AGG  AAC  CGT  AAG  AAA
          S    S    S    P    F    Q    L    Y    Y    F    I    S    L    A    F    F>
```

FIG. 3-3

```
         870           880           890           900           910
     *    *    *    *    *    *    *    *    *    *
    GGA  TTC  TTA  ATT  CCA  TTT  GTG  CTT  ATC  ATC  TAC  TGC  TAT  GCA  GCC  ATC
    CCT  AAG  AAT  TAA  GGT  AAA  CAC  GAA  TAG  TAG  ATG  ACG  ATA  CGT  CGG  TAG
     G    F    L    I    P    F    V    L    I    I    Y    C    Y    A    A    I>
              920           930           940           950           960
          *    *    *    *    *    *    *    *    *    *
    ATC  CGG  ACA  CTT  AAT  GCA  TAC  GAT  CAT  AGA  TGG  TTG  TGG  TAT  GTT  AAG
    TAG  GCC  TGT  GAA  TTA  CGT  ATG  CTA  GTA  TCT  ACC  AAC  ACC  ATA  CAA  TTC
     I    R    T    L    N    A    Y    D    H    R    W    L    W    Y    V    K>
                   970           980           990          1000
               *    *    *    *    *    *    *    *    *
    GCG  AGT  CTC  CTC  ATC  CTT  GTG  ATT  TTT  ACC  ATT  TGC  TTT  GCT  CCA  AGC
    CGC  TCA  GAG  GAG  TAG  GAA  CAC  TAA  AAA  TGG  TAA  ACG  AAA  CGA  GGT  TCG
     A    S    L    L    I    L    V    I    F    T    I    C    F    A    P    S>
   1010          1020          1030          1040          1050
     *    *    *    *    *    *    *    *    *    *
    AAT  ATT  ATT  CTT  ATT  ATT  CAC  CAT  GCT  AAC  TAC  TAC  TAC  AAC  AAC  ACT
    TTA  TAA  TAA  GAA  TAA  TAA  GTG  GTA  CGA  TTG  ATG  ATG  ATG  TTG  TTG  TGA
     N    I    I    L    I    I    H    H    A    N    Y    Y    Y    N    N    T>
   1060          1070          1080          1090          1100
     *    *    *    *    *    *    *    *    *
    GAT  GGC  TTA  TAT  TTT  ATA  TAT  CTC  ATA  GCT  TTG  TGC  CTG  GGT  AGT  CTT
    CTA  CCG  AAT  ATA  AAA  TAT  ATA  GAG  TAT  CGA  AAC  ACG  GAC  CCA  TCA  GAA
     D    G    L    Y    F    I    Y    L    I    A    L    C    L    G    S    L>
        1110          1120          1130          1140          1150
     *    *    *    *    *    *    *    *    *    *
    AAT  AGT  TGC  TTA  GAT  CCA  TTC  CTT  TAT  TTT  CTC  ATG  TCA  AAA  ACC  AGA
    TTA  TCA  ACG  AAT  CTA  GGT  AAG  GAA  ATA  AAA  GAG  TAC  AGT  TTT  TGG  TCT
     N    S    C    L    D    P    F    L    Y    F    L    M    S    K    T    R>
             1160          1170          1180          1190          1200
          *    *    *    *    *    *    *    *    *    *
    AAT  CAC  TCC  ACT  GCT  TAC  CTT  ACA  AAA  TAG  TGA  AAT  GAT  CTT  AGA  GAA
    TTA  GTG  AGG  TGA  CGA  ATG  GAA  TGT  TTT  ATC  ACT  TTA  CTA  GAA  TCT  CTT
     N    H    S    T    A    Y    L    T    K    *    *    N    D    L    R    E>
                  1210          1220
               *    *    *    *
    CAA  GGA  CAG  CCA  TCA  CAG  AGA  ACG
    GTT  CCT  GTC  GGT  AGT  GTC  TCT  TGC
     Q    G    Q    P    S    Q    R    T>
```

FIG. 4-1

```
              10         20         30         40         50
               *          *          *          *          *
          -ACAGGCATG GAAAATGATA CAAACAACTT GGCAAAGCCA ACCTTACCCA
              60         70         80         90        100
               *          *          *          *          *
          TTAAGACCTT TCGTGGAGCT CCCCCAAATT CTTTTGAAGA GTTCCCCTTT
             110        120        130        140        150
               *          *          *          *          *
          TCTGCCTTGG AAGGCTGGAC AGGAGCCACG ATTACTGTAA AAATTAAGTG
             160        170        180        190        200
               *          *          *          *          *
          CCCTGAAGAA AGTGCTTCAC ATCTCCATGT GAAAAATGCT ACCATGGGGT
             210        220        230        240        250
               *          *          *          *          *
          ACCTGACCAG CTCCTTAAGT ACTAAACTGA TACCTGCCAT CTACCTCCTG
             260        270        280        290        300
               *          *          *          *          *
          GTGTTTGTAG TTGGTGTCCC GGCCAATGCT GTGACCCTGT GGATGCTTTT
             310        320        330        340        350
               *          *          *          *          *
          CTTCAGGACC AGATCCATCT GTACCACTGT ATTCTACACC AACCTGGCCA
             360        370        380        390        400
               *          *          *          *          *
          TTGCAGATTT TCTTTTTTGT GTTACATTGC CCTTTAAGAT AGCTTATCAT
             410        420        430        440        450
               *          *          *          *          *
          CTCAATGGGA ACAACTGGGT ATTTGGAGAG GTCCTGTGCC GGGCCACCAC
             460        470        480        490        500
               *          *          *          *          *
          AGTCATCTTC TATGGCAACA TGTACTGCTC CATTCTGCTC CTTGCCTGCA
             510        520        530        540        550
               *          *          *          *          *
          TCAGCATCAA CCGCTACCTG GCCATCGTCC ATCCTTTCAC CTACCGGGGC
             560        570        580        590        600
               *          *          *          *          *
          CTGCCCAAGC ACACCTATGC CTTGGTAACA TGTGGACTGG TGTGGGCAAC
             610        620        630        640        650
               *          *          *          *          *
          AGTTTTCTTA TATATGCTGC CATTTTTCAT ACTGAAGCAG GAATATTATC
```

FIG. 4-2

```
              660         670         680         690         700
               *  *        *  *        *  *        *  *        *  *
          TTGTTCAGCC  AGACATCACC  ACCTGCCATG  ATGTTCACAA  CACTTGCGAG 710         720         730         740         750
               *  *        *  *        *  *        *  *        *  *
          TCCTCATCTC  CCTTCCAACT  CTATTACTTC  ATCTCCTTGG  CATTCTTTGG 760         770         780         790         800
               *  *        *  *        *  *        *  *        *  *
          ATTCTTAATT  CCATTTGTGC  TTATCATCTA  CTGCTATGCA  GCCATCATCC 810         820         830         840         850
               *  *        *  *        *  *        *  *        *  *
          GGACACTTAA  TGCATACGAT  CATAGATGGT  TGTGGTATGT  TAAGGCGAGT 860         870         880         890         900
               *  *        *  *        *  *        *  *        *  *
          CTCCTCATCC  TTGTGATTTT  TACCATTTGC  TTTGCTCCAA  GCAATATTAT 910         920         930         940         950
               *  *        *  *        *  *        *  *        *  *
          TCTTATTATT  CACCATGCTA  ACTACTACTA  CAACAACACT  GATGGCTTAT 960         970         980         990         1000
               *  *        *  *        *  *        *  *        *  *
          ATTTTATATA  TCTCATAGCT  TTGTGCCTGG  GTAGTCTTAA  TAGTTGCTTA 1010        1020        1030        1040        1050
               *  *        *  *        *  *        *  *        *  *
          GATCCATTCC  TTTATTTTCT  CATGTCAAAA  ACCAGAAATC  ACTCCACTGC 1060        1070        1080        1090        1100
               *  *        *  *        *  *        *  *        *  *
          TTACCTTACA  AAATAGTGAA  ATGATCTTAG  AGAACAAGGA  CAGCCATCAC

AGA
```

FIG. 5A

```
hPAR3-1    MKA    LIFAAAGLLLLLP TFCQSGMENDINNLAKP TLPIK/TFRGAPPN SFEEFPFSALEGWTGATITVKIKC    PEESASHLHVKNAIMG
hPAR1-1    MGPRR  LLLVAACFSLCGP LLSARTRARRPESKATNATLDPR/SFLLRNPNDKYEPFWEDEEKNESGL TEYRLVSINKSSPLQKQLPAFISEDASG
hPAR2-1    MRSPSAAWLLGAAILLA ASLSCSGTIQG         TNRSSKGR/SLIGKVDGTSHVTGKGVTV                        ETVFSVDEFSAS

|--------TM1-------|                                |--------TM2---------|             |-------TM3--------|
hPAR3-87   YLTSSLSTKLIPAIYLLVFVVGVPANAVTLWMLFFRTR SICTTVFYTNLAIADFLFCVTLPFKIAYHLNGNNWVFGEVLCRATTVIFYGNMYCSILLLACISINRYLAI
hPAR1-95   YLTSSWLTLFVPSVYTGVFVVSLPLNIMAIVVFILKMKVKPAVVYMLHLATADVLFVSVLPFKISYYFSGSDWQFGSELCRFVTAAFYCNMYASILLMTVISIDRFLAV
hPAR2-68   VLTGKLTTVFLPIVYTIVFVVGLPSNGMALWVFLFRTKKKHPAVIYMANLALADLLSVIWFPLKIAYHIHGNNWIYGEALCNVLIGFFYGNMYCSILFMTCLSVQRYWVI

|-------TM4-------|                          |--------TM5--------|
hPAR3-196  VHPFTYRGLPKHTYALVTCGLVWATVFLYMLPFFILKQEYLVQPDITTCHDVHNTCESSSPFQLYYFISLAFFGFLIPFVLIIYCYAAIIRTLNA       YDHRWLWYV
hPAR1-205  VYPMQSLSWRTLGRASFTCLAIWALAIAGVVPLVLKEQTIQVPGLNITTCHDVLNETLLEG YYAYYFSAFSAVFFFVPLIISTVCYCSIIRCLSSSAVANRSKK SRAL
hPAR2-178  VNPMGHSRKKANIAIGI SLAIWLLILLVTIPLYVVKQTIFIPALNITTCHDVLPEQLLVGD MFNYFLSLAIGVFLFPAFLTASAYVLMIRMLRSSAMDENSEKKRKRAI

|-----------TM6-----------|                               |-------TM7--------|
hPAR3-301  KASLLILVIFTICFAPSNIILIIHHANYYYNNI DGLYFIYLIALCLGSLNSCLDPFLYFLMSKTRNHSTAYLTK
hPAR1-313  FLSAAVFCIFIICFGPTNVLLIAHYSFLSHTSTTEAAYFAYLLCVCVSSISSCIDPLIYYASSECQRYVYSILCCKESSDPSSYNSSGQLMASKMDTCSSNLNSIYKFLLT
hPAR2-287  KLIVTVLAMYLICFTPSNLLLVHY FLIKSQGQSHVYALYIVALCLSTLNSCIDPFVYYFVSHDFRDHAKNALLCRSVRTVKQMQVSLTSKKHSRKSSSYSSSSTTVKTSY
```

FIG. 5B

```
Hirudin C-tail          ..DFEEIPEEYLQ
hPAR3- 34-62 ..TLPIK / TFRGAPPN SFEEFPFSALEGWTGA...
hPAR1- 37-65 ..TLDPR / SFLLRNPNDKYEPFWEDEEKNESG...
hPAR2- 32-62 ..SSKGR / SLIGKVDGTSHVTGKGVTETVFSVD..
```

DNA ENCODING A PROTEASE-ACTIVATED RECEPTOR 3

FIELD OF THE INVENTION

This invention relates to nucleic acids, their encoded protease-activated receptor 3 proteins, and screening assays for agonists and antagonists of the protease activated receptor 3 proteins.

BACKGROUND OF THE INVENTION

Thrombin, a coagulation protease generated at sites of vascular injury, activates platelets, leukocytes, and mesenchymal cells (Vu, T.-K. H. et al. (1991) Cell 64:1057–1068). Activation of platelets by thrombin is thought to be critical for hemostasis and thrombosis. In animal models, thrombin inhibitors block platelet-dependent thrombosis, which is the cause of most heart attacks and strokes in humans. Available data in humans suggests that thrombosis in arteries can be blocked by inhibitors of platelet function and by thrombin inhibitors. Thus it is likely that thrombin's actions on platelets contribute to the formation of clots that cause heart attack and stroke. Thrombin's other actions on vascular endothelial cells and smooth muscle cells, leukocytes, and fibroblasts may mediate inflammatory and proliferative responses to injury, as occur in normal wound healing and a variety of diseases (atherosclerosis, restenosis, pulmonary inflammation (ARDS), glomerulosclerosis, etc.). A thorough understanding of how thrombin activates cells is an important goal.

A receptor that mediates thrombin signaling has been previously identified (Vu, T.-K. H. et al. (1991) Cell 64:1057–1068, U.S. Pat. No. 5,256,766). This receptor revealed a novel proteolytic mechanism of activation and is referred to as PAR1 (protease-activated receptor 1). PAR1 is activated by the binding of thrombin to and cleavage of PAR1's amino terminal exodomain at a specific site. Receptor cleavage unmasks a new amino terminus, which then functions as a tethered peptide ligand by binding intramolecularly to the body of the receptor to effect transmembrane signaling (Vu, T.-K. H. et al. (1991) Cell 64:1057–1068). Synthetic peptides that mimic this tethered ligand domain function as PAR1 agonists and activate it independent of thrombin and receptor cleavage (Vu, T.-K. H. et al. (1991) Cell 64:1057–1068).

To identify which of thrombin's known cellular actions are mediated by PAR1, a PAR1 knockout mouse was recently generated (Connolly, A. et al. (1996) Nature 381:516–519). Analysis of mice in which both alleles of the PAR1 gene were disrupted provided definitive evidence for a second platelet thrombin receptor and for tissue specific roles of distinct thrombin receptors. Specifically, in mice, PAR1 is not important for platelet responses but is critical for fibroblast responses.

A second protease-activated receptor (PAR2) was cloned during a search for relatives of the Substance K receptor (Nystedt, S., et al. (1994) PNAS USA, 91:9208–9212). The physiological activator of PAR2 remains unknown; it is not activated by thrombin.

SUMMARY OF THE INVENTION

The protease-activated receptor (PAR3) disclosed herein is useful in assaying libraries of compounds for their activity as thrombin agonists and antagonists. DNA encoding PAR3 is placed in a functional expression vector, expressed in a cell line, and used to assay compounds for activity as an agonist or antagonist of thrombin's affect on PAR3.

The invention features substantially pure DNA (cDNA or genomic DNA) encoding a protease-activated receptor 3 (PAR3) from vertebrate tissues (SEQ ID NO:1, SEQ ID NO:2, SEQ ID NO:4 and SEQ ID NO:5) and degenerate sequences thereof; substantially pure protease-activated receptor 3 polypeptides encoded thereby; as well as amino acid sequences substantially identical to the amino acid sequences SEQ ID NO:3 and SEQ ID NO:6 from mouse and human, respectively. The invention further comprises fragments of the PAR3 receptor which are activated by thrombin. Such fragments may have the same amino acid sequence as SEQ ID NOs:3 and 6 or be at least 80% identical to the amino acid sequences SEQ ID NO:3 and SEQ ID NO:6.

In various embodiments, the DNA, receptor or receptor fragment is derived from a vertebrate animal, preferably, human or mouse. However, the gene can be chemically synthesized.

An object of the invention is to provide a nucleotide sequence encoding a novel receptor.

Another object is to provide a cell line genetically engineered to express the nucleotide sequence.

Another object is to provide a method whereby a compound or library of compounds can be assayed as thrombin agonists or antagonists for their ability to activate or block the receptor expressed by the nucleotide sequence.

An advantage of the present invention is that a novel thrombin receptor PAR3 is disclosed making it possible to identify novel thrombin agonists and antagonists which may not be identifiable via PAR1 or PAR2 receptors.

A feature of the invention is that it makes it possible to obtain additional information regarding thrombin activation and the sequence of biochemical events initiated by such.

These and other objects, advantages and features of the present invention will become apparent to those skilled in the art upon reading the disclosure.

BRIEF DESCRIPTION OF THE DRAWINGS

FIG. 1 is the complete nucleotide and amino acid sequences (SEQ ID NO:1 and SEQ ID NO:3, respectively) of the mouse protease-activated receptor 3 gene coding region cDNA. The deduced amino acid sequence of the receptor is provided below the nucleotide sequence and contains 369 amino acids. The deduced amino acid sequence begins at nucleotides 51–53 (ATG=Met) and ends at nucleotides 1158–1160 (TAG=stop).

FIG. 2 is the genomic sequence (containing exon 2) of the mouse protease-activated receptor 3 (SEQ ID NO:2).

FIG. 3 is the nucleotide and deduced amino acid sequences (SEQ ID NO:4 and SEQ ID NO:6, respectively) of the human protease-activated gene coding region cDNA. The deduced amino acid sequence is provided below the nucleotide sequence and contains 374 amino acids. The coding region of the cDNA sequence begins at nucleotides 58–60 (ATG=Met) and ends at nucleotides 1180–1182 (TAG=stop).

FIG. 4 is the genomic sequence (containing exon 2) of the human protease-activated receptor 3 (SEQ ID NO:5).

FIG. 5A show the alignment of the deduced amino acid sequences of the human PAR3 gene (SEQ ID NO:6), the human PAR1 gene (SEQ ID NO:7),and the human PAR2 gene (SEQ ID NO:8). Blank spaces have been introduced into the sequence to provide better alignment for purposes of homology comparison. Transmembrane domains are overlined (TM1–7). FIG. 5B shows the alignment of the C-tail of Hirudin (SEQ ID NO:9) with human PAR1, PAR2, and PAR3 amino acid sequences.

DESCRIPTION OF THE PREFERRED EMBODIMENTS

Figure 6:
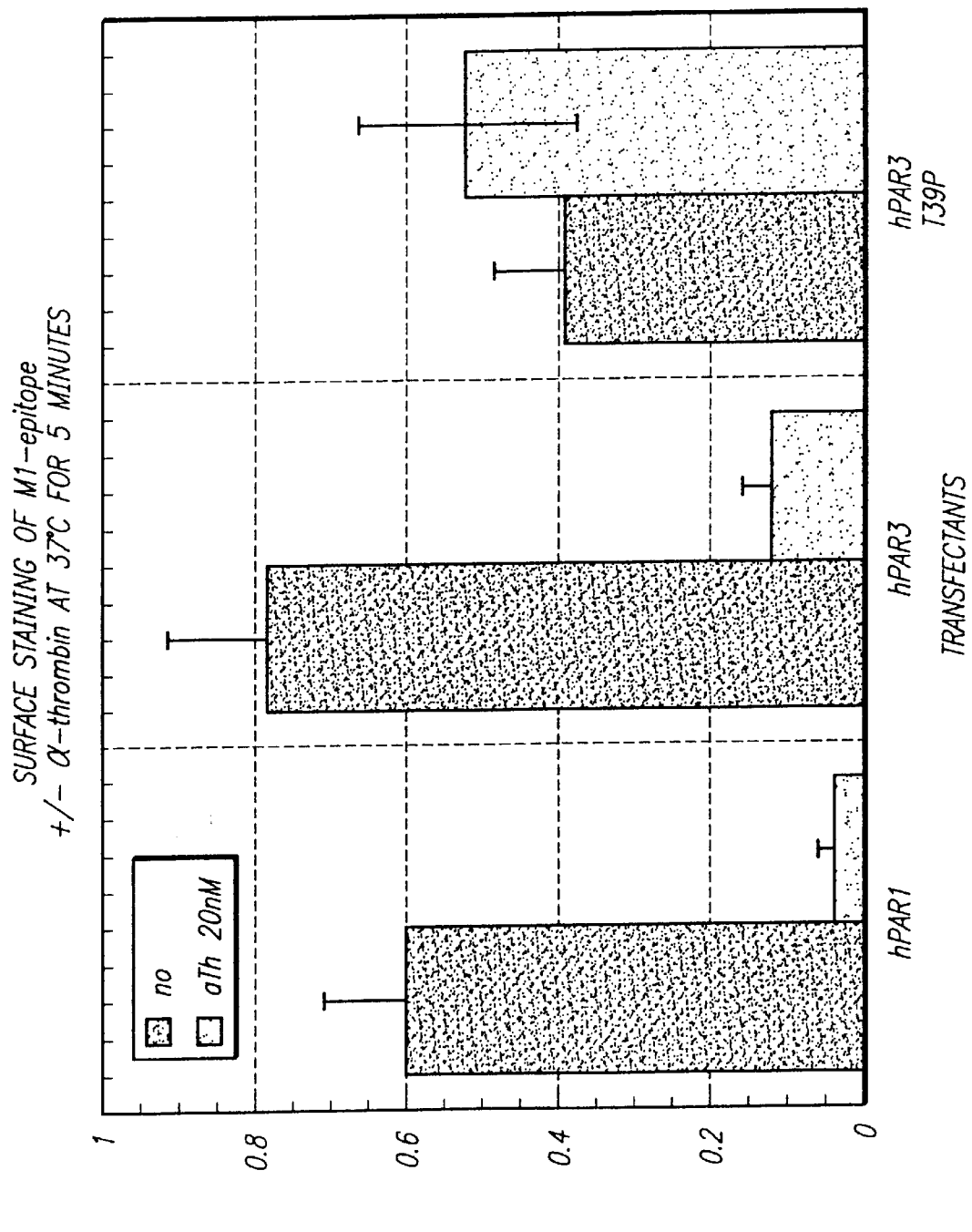
FIG. 6 is a bar graph showing cell surface binding of M1 monoclonal antibody to M1 epitope on Cos 7 cells expressing hPAR3 or hPAR3 T39P in the presence and absence of α-thrombin.

Before the present protease-activated receptor assays and methods of using such are described, it is to be understood that this invention is not limited to the particular DNA sequences, materials, methods, or processes described as such may, of course, vary. It is also to be understood that the terminology used herein is for the purpose of describing particular embodiments only, and is not intended to be limiting since the scope of the present invention will be limited only by the appended claims.

It must be noted that as used in this specification and the appended claims, the singular forms "a", "and," and "the" include plural referents unless the contexts clearly dictates otherwise. Thus, for example, reference to "a DNA sequence" includes mixtures and large numbers of such sequences, reference to "an assay" includes assays of the same general type, and reference to "the method" includes one or more methods or steps of the type described herein.

The publications discussed herein are provided solely for their disclosure prior to the filing date of the present application. Nothing herein is to be construed as an admission that the present invention is not entitled to antedate such publication by virtue of prior invention.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications cited herein are incorporated herein by reference for the purpose of disclosing and describing specific aspects of the invention for which the publication is cited in connection with.

DEFINITIONS

By "protease-activated receptor 3", "PAR3", "PAR3 receptor" and the like, is meant all or part of a vertebrate cell surface protein which is specifically activated by thrombin or a thrombin agonist thereby activating PAR3-mediated signalling events (e.g., phosphoinositide hydrolysis, $Ca^{2+}$ efflux, platelet aggregation). The polypeptide is characterized as having the ligand activating properties (including the agonist activating and antagonist inhibiting properties) and tissue distribution described herein. Specifically, PAR3 receptors are expressed by the DNA sequences of SEQ ID NOs:2, 4, and 5.

By a "polypeptide" is meant any chain of amino acids, regardless of length or post-translational modification (e.g., glycosylation).

By "substantially pure" is meant that the protease-activated receptor 3 polypeptide provided by the invention is at least 60%, by weight, free from the proteins and naturally-occurring organic molecules with which it is naturally associated. Preferably, the preparation is at least 75%, more preferably at least 90%, and most preferably at least 99%, by weight, PAR3 polypeptide. A substantially pure PAR3 polypeptide may be obtained, for example, by extraction from a natural source, by expression of a recombinant nucleic acid encoding a PAR3 polypeptide, or by chemically synthesizing the protein. Purity can be measured by any appropriate method, e.g., column chromatography, polyacrylamide gel electrophoresis, or HPLC analysis. The protein is substantially pure if it can be isolated to a band in a gel.

By a "substantially identical" amino acid sequence is meant an amino acid sequence which differs only by conservative amino acid substitutions, for example, substitution of one amino acid for another of the same class (e.g., valine for leucine, arginine for lysine, etc.) or by one or more non-conservative amino acid substitutions, deletions, or insertions located at positions of the amino acid sequence which do not destroy the biological activity of the receptor. Such equivalent receptors can be isolated by extraction from the tissues or cells of any animal which naturally produce such a receptor or which can be induced to do so, using the methods described below, or their equivalent; or can be isolated by chemical synthesis; or can be isolated by standard techniques of recombinant DNA technology, e.g., by isolation of cDNA or genomic DNA encoding such a receptor. Substantially identical receptors have the same biological function, e.g. are activated by the same compound.

By "derived from" is meant encoded by the genome of that organism and present on the surface of a subset of that organism's cells.

By "isolated DNA" is meant DNA that is not in its native environment in terms of not being immediately contiguous with (i.e., covalently linked to) the complete coding sequences with which it is immediately contiguous (i.e., one at the 5' end and one at the 3' end) in the naturally-occurring genome of the organism from which the DNA of the invention is derived. The term therefore includes, for example, recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes any recombinant DNA which is part of a hybrid gene encoding additional polypeptide sequence.

"Isolated DNA" can mean the DNA is in vectors which are preferably capable of directing expression of the protein encoded by the DNA in a vector-containing cell and further includes cells containing such vectors (preferably eukaryotic cells, e.g., CHO cells (ATCC; Cat. No. CCL 61 or COS-7 cells (ATCC; Cat. No. CRL 1651; and the Xenopus oocytes of the type described in the above cited reference Vu, T.-K. H. et al. (1991) Cell 64:1057–1068). Preferably, such cells are stably transfected with such isolated DNA.

By "transformed cell" and "transfected cell", "genetically engineered cell", and the like, is meant a cell into which (or into an ancestor of which) has been introduced, by means of genetic engineering, a DNA molecule encoding a PAR3 (or DNA encoding a biologically active fragment or analog, thereof). Such a DNA molecule is "positioned for expression" meaning that the DNA molecule is positioned adjacent to a DNA sequence which directs transcription and translation of the sequence (i.e., facilitates the production of the PAR3 protein, or fragment or analog, thereof).

By "specifically activates", as used herein, is meant an agent, such as thrombin, a thrombin analog, a PAR3 agonist or other chemical agent including polypeptides such as an antibody, which activates protease-activated receptor 3, receptor polypeptide or a fragment or analog thereof to initiate PAR3-mediated biological events as described herein, but which does not substantially bind other molecules in a sample, e.g., a biological sample, which naturally includes a protease-activated receptor 3 polypeptide.

By "specifically inhibits", as used herein, is meant an agent, such as a thrombin analog, a PAR3 antagonist or other chemical agent including polypeptides such as an antibody, which inhibits activation of protease-activated receptor 3, receptor polypeptide or a fragment or analog thereof, such as by inhibiting thrombin or by blocking activation of PAR3 by thrombin or other PAR3 activator. Preferably, the agent activates or inhibits the biological activity in vivo or in vitro of the protein to which it binds.

By "biological activity" is meant the ability of the protease-activated receptor 3 to bind thrombin or a PAR3 agonist and signal the appropriate cascade of biological events (e.g., phosphoinositide hydrolysis, $Ca^{2+}$ efflux, and platelet aggregation, and the like, as described herein.

By "substantial increase" is meant an increase in activity or other measurable phenotypic characteristic that is at least approximately a 2-fold increase over control level (where control assays are performed in the absence of activator), preferably at least approximately a 5-fold increase, more preferably at least approximately a 10-fold increase in activity over a control assay.

By "substantial decrease" or "substantial reduction" is meant a decrease or reduction in activity or other measurable phenotypic characteristic that is approximately 80% or the control level, preferably reduced to approximately 50% of the control level, or more preferably reduced to approximately 10% or less of the control level.

The terms "screening method" and "assay method" are used to describe a method of screening a candidate compound for its ability to act as an agonist of a PAR3 ligand. The method involves: a) contacting a candidate agonist compound with a recombinant protease-activated receptor 3 (or PAR3 agonist-binding fragment or analog); b) measuring activation of the receptor, the receptor polypeptide or the receptor fragment or analog; and c) identifying agonist compounds as those which interact with the recombinant receptor and trigger PAR3 activation. Interaction may be cleavage of the receptor to unmask an intramolecular receptor activating peptide or by mimicking the intramolecular receptor-activating peptide. A tethered ligand may be more difficult to block than a free agonist. Thus, blocking thrombin is the acid test for an agonist which will block responses by other thrombin substrates.

By an "agonist" is meant a molecule which mimics a particular activity, in this case, interacting with a PAR3 ligand in a manner which activates thereby triggering the biological events which normally result from the interaction (e.g., phosphoinositide hydrolysis, $Ca^{2+}$ efflux, and platelet aggregation). Preferably, an agonist initiates a substantial increase in receptor activity relative to control assays in the absence of activator or candidate agonist. An agonist may possess the same, less, or greater activity than a naturally-occurring PAR3 ligand.

The terms "antagonist assay", "antagonist screening" and the like, refer to a method of screening a candidate compound for its ability to antagonize interaction between a naturally-occurring activating ligand or an agonist and the PAR3. The method involves: a) contacting a candidate antagonist compound with a first compound which includes a recombinant PAR3 (or agonist-binding fragment or analog) on the one hand and with a second compound which includes thrombin or a PAR3 agonist on the other hand; b) determining whether the first and second compounds interact or are prevented from interaction by the candidate compound; and c) identifying antagonistic compounds as those which interfere with the interaction of the first compound (PAR3 receptor) to the second compound (PAR3 agonist) and which thereby substantially reduce thrombin or PAR3 agonist-activated biological events (e.g., phosphoinositide hydrolysis, $Ca^{2+}$ efflux, and platelet aggregation).

By an "antagonist" is meant a molecule which blocks activation of a PAR3 receptor. This can be done by inhibiting a particular activity such as the ability of thrombin, for example, to interact with a protease-activated receptor 3 thereby triggering the biological events resulting from such an interaction (e.g., phosphoinositide hydrolysis, $Ca^{2+}$ efflux, and platelet secretion, or platelet aggregation). An antagonist may bind to and thereby block activation of a PAR3 receptor.

The terms "treatment", "treating", "treat" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particular a human, and includes:

(a) preventing the disease or symptom from occurring in a subject which may be predisposed to the disease or symptom but has not yet been diagnosed as having it;

(b) inhibiting the disease symptom, i.e., arresting its development; or (c) relieving the disease symptom, i.e., causing regression of the disease.

PREFERRED EMBODIMENTS

In preferred embodiments of both screening methods, the recombinant PAR3 is stably expressed by a vertebrate cell which normally presents substantially no PAR3 on its surface (i.e., a cell which does not exhibit any significant thrombin-mediated phosphoinositide hydrolysis or $Ca^{2+}$ efflux in the presence of a PAR activator); the vertebrate cell is a mammalian cell, is a Rat 1 cell, or a COS 7 cell; and the candidate antagonist or candidate agonist is a thrombin analog, PAR3 peptide fragment or analog or other chemical agent including a polypeptide such as an antibody.

The receptor proteins of the invention are likely involved in the activation of vertebrate platelet, leukocyte, and mesenchymal cells in response to wounding, as well as mediating signalling in embryonic development. Such proteins and in particular PAR3 antagonists are useful therapeutics for the treatment of such conditions as thrombosis, atherosclerosis, restenosis, and inflammation associated with normal wound healing and a variety of diseases including atherosclerosis, restenosis, pulmonary inflammation (ARDS) and glomerulosclerosis. Preferred therapeutics include 1) agonists, e.g., thrombin analogs, PAR3 peptide fragments or analogs thereof, or other compounds which mimic the action of thrombin upon interaction with the protease-activated receptor 3 or mimic the action of an intramolecular receptor activating peptide; and 2) antagonists, e.g., thrombin analogs, antibodies, or other compounds, which block thrombin or protease-activated receptor 3 function by interfering with the thrombin:receptor interaction or by interfering with the receptor intramolecular activating peptide. The dosage would be expected to be comparable with current antiflammatory drugs and should be adjusted based on the age, sex, weight and condition of the patient beginning with small doses and increasing gradually based on responsiveness and toxicity.

Because the receptor component may now be produced by recombinant techniques and because candidate agonists and antagonists may be screened using transformed, cultured cells, the instant invention provides a simple and rapid approach to the identification of useful therapeutics. Isolation of the PAR3 gene (as cDNA or genomic DNA) allows its expression in a cell type which does not normally bear PAR3 on its surface, providing a system for assaying a thrombin:receptor interaction and receptor activation.

EXAMPLES

The following examples are put forth so as to provide those of ordinary skill in the art with a complete disclosure and description of how to make receptor proteins and sequences encoding such proteins and carry out the methodology for finding such DNA sequences and proteins, and are not intended to limit the scope of what is regarded as the invention. Efforts have been made to insure accuracy with respect to numbers used (e.g., amounts, temperature, etc.) but some experimental errors and deviations should be accounted for. Unless indicated otherwise, parts or parts by weight, molecular weight is weight average molecular weight; temperature is in degrees centigrade; and pressure is at or near atmospheric.

There now follows a description of the cloning and characterization of the cDNA, genomic DNA and the receptor protein of the protease-activated receptor 3 from mouse and human. Expression vectors containing and capable of expressing the PAR3 DNA, as well as transformed cells containing and expressing the DNA of the invention are also described. Also described are possible PAR3 agonists and antagonists as well as screening assays for receptor agonists and receptor antagonists.

Example 1
Isolation of the Mouse Protease-Activated Receptor 3

Rat platelets were used as a source of RNA in the search for and cloning of PAR3 because rat platelets are more abundant than mouse platelets and, like mouse platelets, they do not respond to PAR1 agonist peptides (Connolly, A. et al. (1996) Nature 381: 516–519; and Connolly, T. M. et al (1994) Thromb Haemost 72: 627–33).

Total RNA was prepared from rat platelets using Trizol reagent (Gibco BRL). cDNA was then prepared using random hexamer primers and the Superscript reverse transcriptase system (Gibco, BRL). cDNA was then used as template for PCR amplification using a Robocycler Gradient 96® (Stratagene) and the primers 5'-GTTTACATGCTI(A/C)AC(C/T)TIGCI(A/C/G/T)TIGC(A/C/G/T)GA-3' (SEQ ID NO:10) and 5'-GGATAIACIACIGCIA(A/G/T)(A/G)(A/T)AIC(G/T)(A/C/G/T)TC-3' (SEQ ID NO:11) at 5 μM in 20 μM Tris-HCl (pH 8.4), 50 μM KCl, 1.5 μM MgCl2, 0.2 μM dNTP, and 50 U/μl Taq polymerase. Polymerase chain reaction temperature was varied as follows: 94° C. for 4 min; 30 cycles of 94° C. for 45 sec, 39° C. for 60 sec, and 72° C. for 90 sec; then 72° C. for 7 min. PCR products were subcloned using the TA cloning kit (InVitrogen, San Diego, Calif.). Rat cDNA clones with inserts of approximately 200 bp were analyzed by nucleic acid sequencing. One sequence predicted a novel G-protein coupled receptor related to PAR1 and PAR2. This sequence was used to obtain mouse and human cDNA and genomic clones by a combination of PCR and hybridization techniques (see, for example, Sambrook, J. et al. (1989) Molecular Cloning: A Laboratory Manual, Cold Spring Harbor Laboratory, N.Y.). The nucleotide sequences are shown in FIGS. 1–4.

The rat PCR product was then used to clone the full length mouse cDNA and genomic DNA clones. The nucleotide sequences and deduced amino acid sequence of the mouse PAR3 are shown in FIGS. 1 and 2.

The human PAR3 cDNA used for the functional studies presented below was cloned from a Lamda gt 10 intestinal cDNA library (Clonetech). Features of human PAR3's amino acid sequence are shown in FIGS. 5A and 5B by alignment of the deduced amino acid sequence of PAR3 with those of PAR1 and PAR2. Predicted transmembrane (TM) domains are overlined and predicted Asn-linked glycosylation sites in PAR3 are underlined in the figure. The amino terminal exodomains are compared in FIG. 5b, including the cleavage site (^), the tethered ligand domains of PAR1 and PAR2, and the predicted tethered ligand domain of PAR3 (underlined). Also underlined is PAR3's hirudin-like domain (FEEFP). The similar FEEIP and YEPFW sequences in hirudin and PAR1, respectively are known to bind thrombin's fibrinogen-binding exosite.

The human PAR3 cDNA contained an open reading frame encoding a 374 amino acid putative G protein-coupled receptor (FIG. 3). BLAST search of the Genbank and EST databases revealed this protein to be novel with 28% and 30% amino acid sequence identity to human PAR1 and PAR2 (FIG. 5a, Table I). Its amino terminal exodomain revealed a possible thrombin cleavage site and a striking hirudin-like sequence (FIG. 5b). Like the carboxyl tail of hirudin itself, PAR1's hirudin-like sequence is known to dock with thrombin's fibrinogen binding exosite, an interaction important for efficient PAR1 cleavage by thrombin (Vu, T.-K. H. et al.(1991) Nature 353:674–677; Liu, L. et al. (1991) J. Biol. Chem 266:16977–16980; Mathews, I. I. et al. (1994) Biochem 33 3266–79; Ishii, K. (1995) J. Biol. Chem 270:16435–16440, which references are herein incorporated by reference in their entirety). These observations strongly suggested that this new receptor was a novel thrombin receptor.

A comparison of PAR deduced amino acid sequences from human, mouse, and Xenopus is provided in Table I below. The % identity of the total sequence as well as the % identity of the transmembrane regions are shown.

TABLE I

| PAR SEQUENCE | % AMINO ACID IDENTITY | |
|---|---|---|
|  | TOTAL | TM1-7 |
| hPAR3 vs hPAR1 | 28 | 37 |
| hPAR3 vs hPAR2 | 30 | 38 |

TABLE I-continued

| PAR SEQUENCE | % AMINO ACID IDENTITY | |
|---|---|---|
| | TOTAL | TM1-7 |
| hPAR1 vs hPAR2 | 28 | 42 |
| hPAR3 vs xPAR1 | 29 | 38 |
| hPAR1 vs xPAR1 | 52 | 63 |
| hPAR3 vs mPAR3 | 67 | 74 |
| hPAR1 vs mPAR1 | 77 | 81 |
| hPAR2 vs mPAR2 | 78 | 85 | h = human  m = mouse  x = Xenopus laevis

Example 2
Polypeptide Expression

Polypeptides according to the invention may be produced by transformation of a suitable host cell with all or part of a PAR3 encoding cDNA fragment (e.g., the cDNAs described above) in a suitable expression vehicle, and expression of the receptor.

Those skilled in the field of molecular biology will understand that any of a wide variety of expression systems may be used to provide the recombinant receptor protein. The precise host cell used is not critical to the invention. The receptor may be produced in a prokaryotic host (e.g., *E. coli*) or in a eukaryotic host (e.g., *Saccharomyces cerevisiae* or mammalian cells, e.g., COS-6M, COS-7, NIH/3T3, or Chinese Hamster Ovary cells). Such cells are available from a wide range of sources (e.g., the American Type Culture Collection, Rockville, Md.). The method of transfection and the choice of expression vehicle will depend on the host system selected. Transformation and mammalian cell transfection methods are described, e.g., in Ausubel et al. (*Current Protocols in Molecular Biology*, John Wiley & Sons, N.Y., (1989)); expression vehicles may be chosen from those provided, e.g., in *Cloning Vectors: A Laboratory Manual* (Pouwels, P. H. et al., (1985), Supp. 1987).

Particularly preferred expression systems are the Xenopus oocyte cells of Vu et al. (Vu et al., Cell (1991) supra) and insect cells (SF9-baculovirus) transfected with an expression vector containing and expressing a receptor protein or biologically active fragment thereof. DNA encoding the human or mouse PAR3 or an appropriate receptor fragment or analog (as described above) is inserted into the expression vector in an orientation designed to allow expression. Alternatively, the PAR3 (or biologically active receptor fragment or analog) is expressed by a stably-transfected mammalian cell line. Other preferable host cells which may be used in conjunction with the expression vehicle include NIH/3T3 cells (ATCC Accession No. 1658). The expression may be used in a screening method of the invention (described below) or, if desired, the recombinant receptor protein may be isolated as described below.

A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the receptor (or receptor fragment or analog) is cloned into an expression vector which includes the dihydrofolate reductase (DHFR) gene. Integration of the plasmid and, therefore, the PAR3-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR cells, ATCC Accession No. CRL 9096) are among the host cells preferred for DHFR selection of a stably-transfected cell line or DHFR-mediated gene amplification.

One particularly preferred stable expression system is a Rat 1 cell (ATCC) stably transfected with a pcDNAI/NEO (InVitrogen, San Diego, Calif.) expression vector.

Expression of the recombinant receptor (e.g., produced by any of the expression systems described herein) may be assayed by immunological procedures, such as Western blot or immunoprecipitation analysis of recombinant cell extracts, or by immunofluorescence of intact recombinant cells (using, e.g, the methods described in Ausubel et al., supra). Recombinant receptor protein is detected using an antibody directed to the receptor. Described below are methods for producing anti-protease-activated receptor 3 antibodies using, as an immunogen, the intact receptor or a peptide which includes a suitable protease-activate receptor 3 epitope. To detect expression of a PAR3 fragment or analog, the antibody is preferably produced using, as an immunogen, an epitope included in the fragment or analog.

Once the recombinant PAR3 protein (or fragment or analog, thereof) is expressed, it is isolated, e.g., using immunoaffinity chromatography. In one example, an anti-PAR3 antibody may be attached to a column and used to isolate intact receptor or receptor fragments or analogs. Lysis and fractionation of receptor-harboring cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, (1980)).

Receptors of the invention, particularly short receptor fragments, can also be produced by chemical synthesis (e.g., by the methods described in *Solid Phase Peptide Synthesis*, (1984) 2nd ed., The Pierce Chemical Co., Rockford, Ill.).

Example 3
Cleavage and Activation Studies of the Recombinant Protease-Activated Receptor 3

PAR3 was demonstrated to be a substrate for thrombin when expressed on the surface of Cos 7 cells (FIG. 6). Human PAR1 or PAR3 cDNAs that were modified to encode receptors displaying a FLAG epitope (amino acid sequence DYKDDD (SEQ ID NO:12) at a site amino to the thrombin cleavage site were transiently expressed in Cos7 cells. Epitope-tagged PAR1 has been previously described (Ishii, K. et al. (1993) J. Biol. Chem. 268:9780–9786). The analogous epitope-tagged PAR3 cDNA was constructed so as to encode a new amino terminus with the sequence MDSKGSSQKGSRLLLLLLVVSNLLLCQGVVS/DYKDDDDVE-TF (SEQ ID NO:13) representing the prolactin signal peptide, putative signal peptidase site (/), FLAG epitope DYKDDDD (SEQ ID NO:12) and junction VE fused to amino acid 17 in PAR 3.

cDNAs were subcloned into the mammalian expression vector pBJ1. For receptor cleavage studies Cos 7 cells were transfected using DEAE-dextran and thrombin-mediated loss of M1 antibody (Kodak) binding to the FLAG epitope of the cell surface using a procedure described by Ishii et al. (Ishii, K. et al. (1993) supra). Over 95% of M1 antibody binding was transfection-dependent in this system. Cells were incubated for 5 min. at 37° C. in the presence (open columns) or absence (closed columns) of 20 nM thrombin (FIG. 6). For biochemical identification of the cleavage site, cleavage of soluble PAR3 amino terminal exodomain by thrombin was assayed as follows. A recombinant PAR3 soluble exodomain was prepared in which the amino terminal exodomain residues 21–94 were sandwiched between a translational start and hexahistidine tag (i.e. MG-[PAR3 21–94]-VEHHHHHH; where VEHHHHHH is SEQ ID NO:18). The recombinant protein was expressed as a soluble polypeptide in *E. coli*, purified, and analyzed before and after thrombin cleavage as previously described for the analogous region of PAR1 (Ishii, K. (1995) J. Biol. Chem. 270:16435–16440). Recombinant soluble amino terminal exodomain was cleaved in solution with 50 nM thrombin for 1 h at 37° C., then analyzed by SDS-PAGE. Even prolonged incubation with a high concentration of thrombin yielded only one detectable cleavage event indicating that only one thrombin cleavage site exists in the PAR3 exodomain. Amino acid sequencing of the cleavage products revealed only a single new amino terminus with the sequence TFRG (see FIG. 1b). Thus, thrombin recognizes and cleaves PAR3 in the amino terminal exodomain between amino acids K38 and T39 with high specificity.

Example 4
PAR3 Signaling Activity

The ability of PAR3 to mediate signaling by thrombin was tested. Xenopus oocytes were microinjected with cRNA encoding epitope-tagged human PAR3 (hPAR3), hPAR3 bearing the T39P cleavage site mutation, or the F40A tethered ligand domain mutation. Thrombin-triggered $^{45}$Ca release was measured as described in Vu et al. (Vu, T.-K. H. et al. (1991) supra). Surface expression of wild type and mutant receptors was confirmed by M1 antibody binding by the method of Ishii, K. et al. (Ishii, K. et al. (1995) J. Biol. Chem. 270:16435–16440; and Ishii, K. et al. (1993) J. Biol. Chem. 268:9780–9786, which references are herein incorporated by reference in their entirety).

Microinjection of Xenopus oocytes with human PAR3 cRNA conferred thrombin-dependent $^{45}$Ca mobilization (FIG. 7) which reflects agonist-triggered phosphoinositide hydrolysis in this system. Mutation of PAR3's thrombin cleavage site ablated thrombin signaling and thrombin rendered proteolytically inactive by the active site inhibitor PPACK failed to activate PAR3 even at concentrations as high as 1 $\mu$M. These data strongly suggest that cleavage of the K 38—T 39 peptide bond is necessary for PAR3 activation by thrombin.

Figure 10:
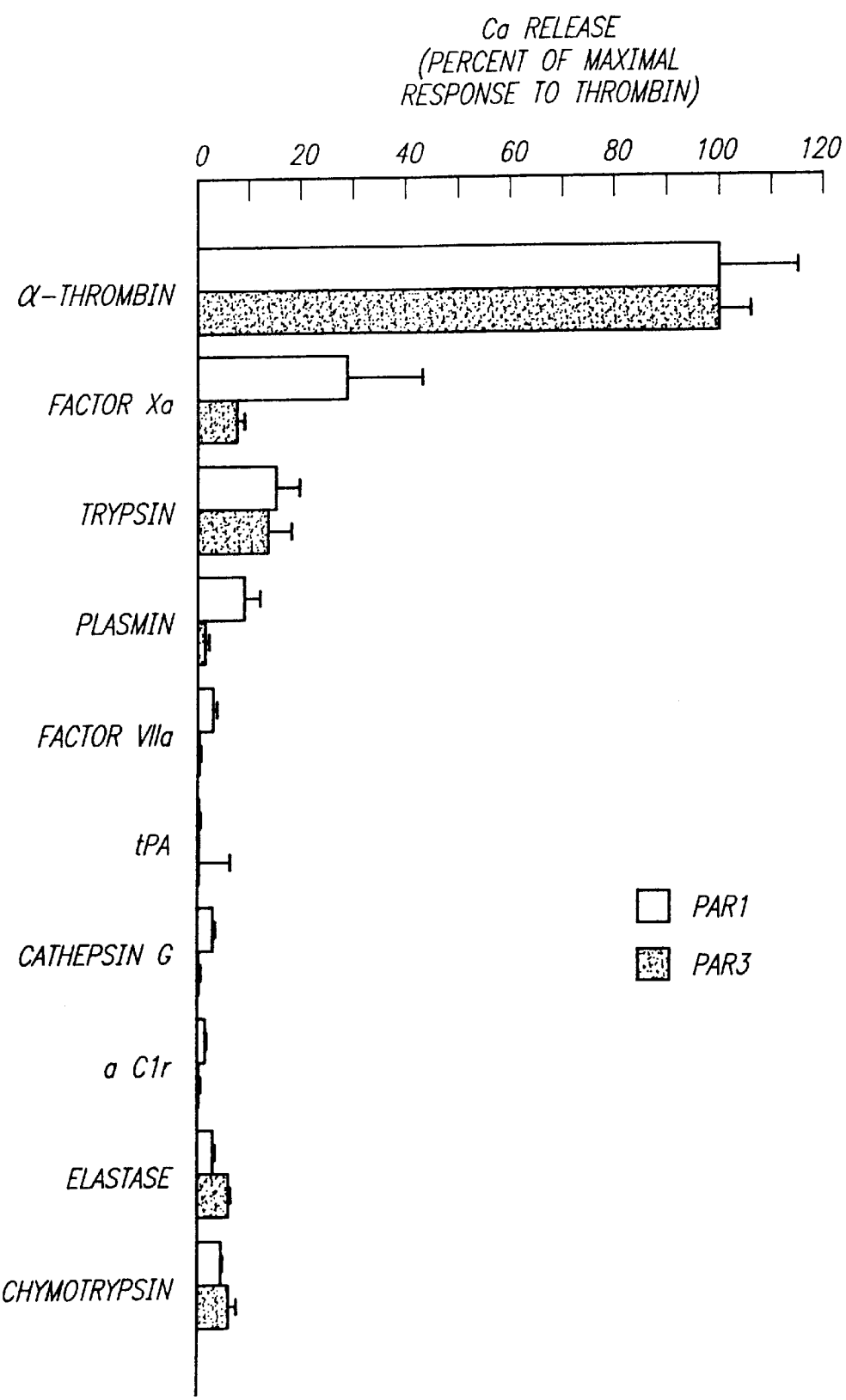
FIG. 10 is a graph comparing the specificity of PAR1 and PAR3 for thrombin.

The specificity of PAR3 and PAR1 signaling was also examined. Protease-triggered $^{45}$Ca release was measured in Xenopus oocytes expressing human PAR1 or PAR3 stimulated with various concentrations of the arginine/lysine specific serine proteases trypsin, Factor Xa, Factor VIIa, tissue plasminogen activator, or plasmin. Chymotrypsin, elastase, and cathepsin G were also tested. PAR3 was at least as specific for thrombin as thrombin receptor PAR1 (FIG. 10).

PAR3 signaling in Cos 7 cells was also examined. Cos 7 cells were transfected with human PAR1 or PAR3. Cells were then metabolically labelled with $^3$H-inositol and phosphoinositide hydrolysis was measured in response to the indicated concentrations of $\alpha$-thrombin (FIG. 8) or $\gamma$-thrombin (FIG. 9) as described by Ishii, et al. and Nanevicz et al. (Ishii, K. et al. (1993) supra; and Nanevicz, T. et al. (1996) J. Biol. Chem. 271:702–706).

Figure 7:
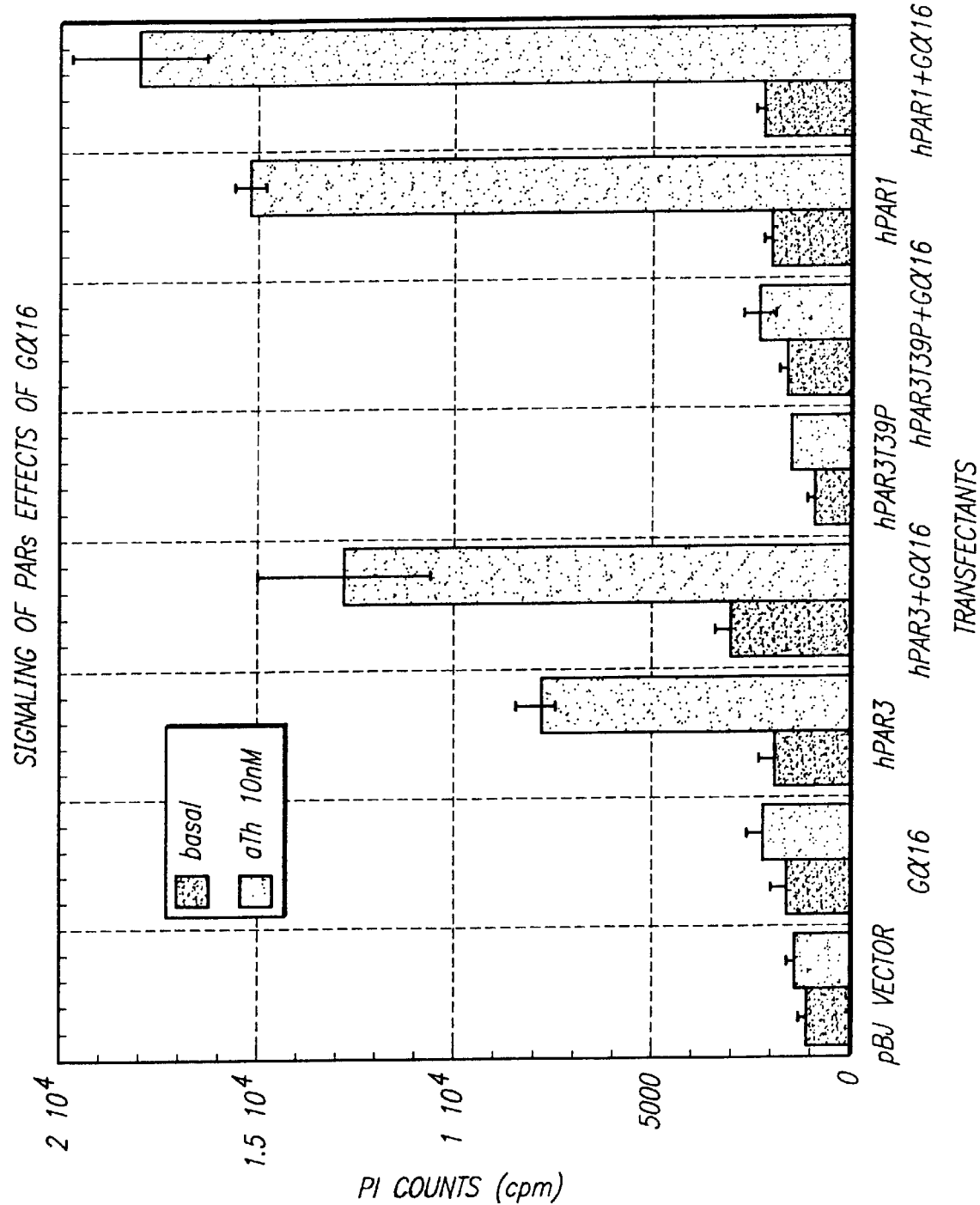
FIG. 7 is a bar graph of hPAR3 signaling in Cos 7 cells in the presence and absence of Gα16 and the presence and absence of α-thrombin. Signaling is measured by phosphoinositide hydrolysis.

Co-transfection with $\alpha$16, a G protein $\alpha$-subunit expressed in hematopoietic cell lines (Amatruda III, T. T. et al. (1991) J. Biol. Chem. 266:5587–5591) caused a 50–150% increase in the maximal PAR3-mediated response to thrombin in these cells in each of three separate experiments (FIG. 7).

Figure 8:
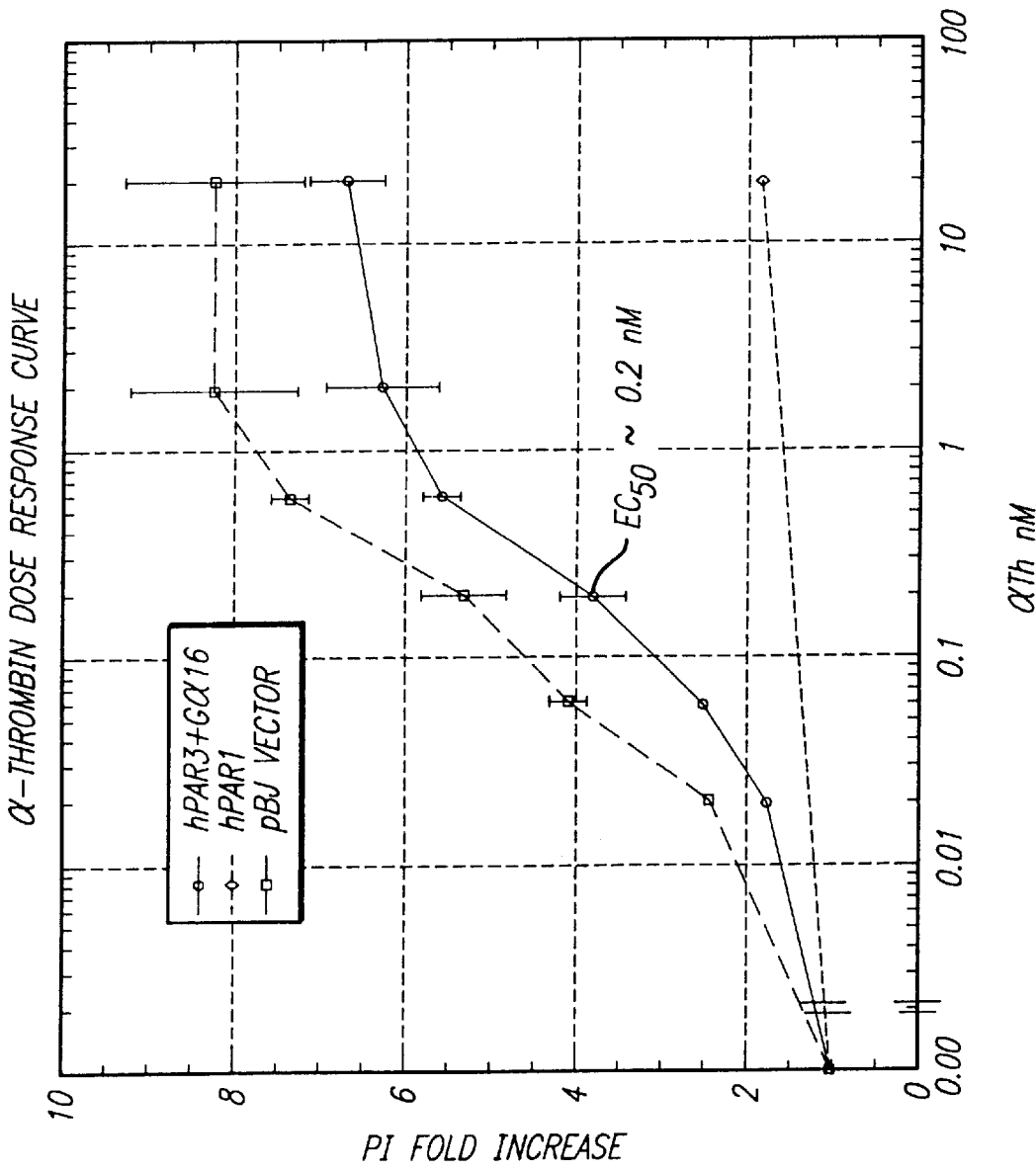
FIG. 8 is a graph of phosphoinositide hydrolysis in response to PAR3 signaling as a function of increasing α-thrombin concentration, and in the presence and absence of Gα16 protein.
Figure 9:
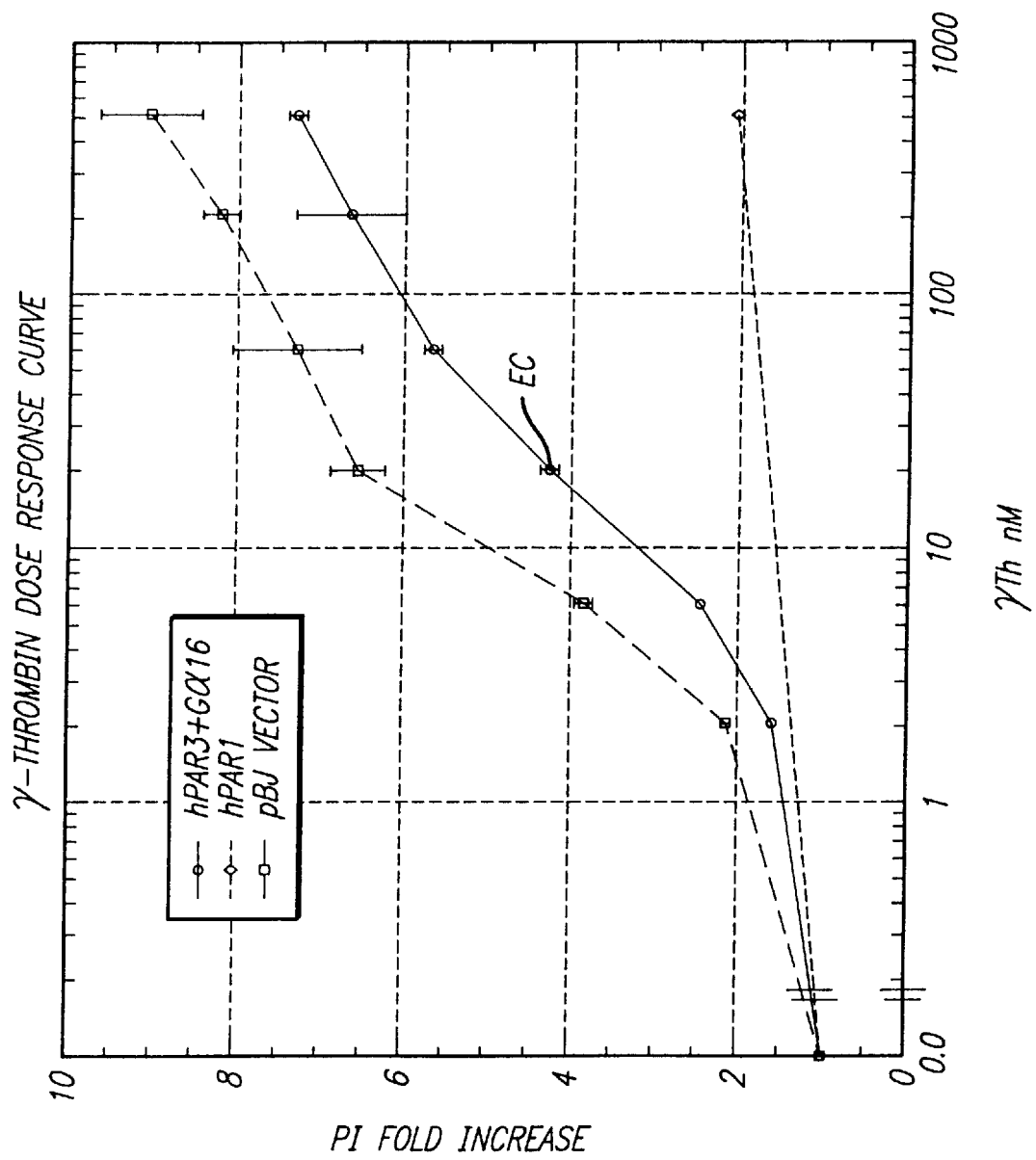
FIG. 9 is a graph of phosphoinositide hydrolysis in response to PAR3 signaling as a function of increasing γ-thrombin concentration, and in the presence and absence of Gα16 protein.

The $EC_{50}$ for thrombin signaling through PAR3 in this system was approximately 0.2 nM, comparable to that seen with PAR1 and well within physiologically achievable thrombin concentrations (FIG. 8). $\gamma$-thrombin, which is defective in its anion-binding exosite (Rydel, T. J. et al. (1994) J. Biol. Chem. 269:22000–22006), was two log units less potent than $\alpha$-thrombin ($EC_{50}$=20 nM; FIG. 9). Similarly, incubation of $\alpha$-thrombin with the fibrinogen binding exosite blocker hirugen (Skrzypczak, J. E. et al. (1991) J. Mol. Biol. 221:1379–1393) right-shifted the dose response curve two logs (not shown). Alanine substitution at F 48 and E 49 in PAR3's hirudin-like sequence, residues predicted to dock with thrombin's fibrinogen-binding exosite by analogy with hirudin and PAR1 (FIG. 5B) also caused a decrease in thrombin signaling by PAR3. These data strongly suggest that PAR3 interacts with thrombin in a manner similar to PAR1 (Mathews, I. I., et al. (1994) Biochem. 33:3266–3279). Specifically, it is likely that PAR3 amino acids 48–52 (FEEFP, SEQ ID NO:14) dock with thrombin's fibrinogen-binding exosite while amino acids 35–38 (LTPK, SEQ ID NO:15) dock with thrombin's active center leading to cleavage of the K 38—T 39 peptide bond.

Synthetic peptides that mimic the new amino terminus unmasked by receptor proteolysis, the so called "tethered ligand domain", act as agonists for PAR1 and PAR2 (Vu, T. K.-H. et al. (1991) Cell 64:1057–1068; Nystedt, S. et al. (1994) PNAS USA 91:9208–9212; and U.S. Pat. No. 5,256, 766, which references are herein incorporated by reference in their entirety).

Peptides homologous to the tethered domain of PAR3 may be tested as potential agonists of PAR3 activity. Two peptides, TFRGAP (SEQ ID NO:16) and TFRGAPPNS (SEQ ID NO:17) were synthesized and tested for their ability to mimic the action of thrombin by causing PAR3 signaling as measured by phosphoinositide hydrolysis. Cos 7 cells expressing human PAR3 were incubated with the peptides at concentrations up to 100 $\mu$M. Phosphoinositide hydrolysis was not observed to be above control levels indicating that the synthetic peptides caused no detectable signaling by PAR3 under these conditions, whereas an $EC_{50}$ of 0.2 nM was determined for $\alpha$-thrombin under the same assay conditions. These results demonstrate that monitoring phosphoinositide hydrolysis provides a useful means for assessing potential agonists for activity on PAR3 signaling for use as potential pharmaceutics.

The tethered ligand domain of PAR3 was required for PAR3 activation by thrombin. Substitution of Ala for Phe 40 (the F40A PAR3 mutant), which is analogous to the critical Phe 43 in PAR1's tethered ligand (Scarborough, R. M. et al. (1992) J. Biol. Chem. 267:13146–13149), ablated PAR3 signaling but not PAR3 cleavage by thrombin. The observation that cleavage of the Lys 38—Thr 39 peptide bond is necessary for PAR3 activation suggests that PAR3 is probably activated by the same tethered ligand mechanism utilized by PAR1 and 2.

Example 5
PAR3 Tissue Expression in Mouse and Human

In situ hybridization of mouse tissue revealed the presence of PAR3 mRNA in megakaryocytes in mouse spleen. In the tissues examined (brain, eye, thymus, heart, lung, liver spleen, pancreas, stomach, small intestine, colon, kidneys, bladder, uterus, ovary, testis, skeletal muscle, peripheral nerve, and skin), megakaryocytes in the spleen were the only cells which displayed clearcut hybridization over background. Control samples in which hybridization was performed with a sense strand probe control were negative for all cells. Northern analysis of mouse tissues for PAR3 mRNA showed signals in spleen and lung, with low levels seen in brain, heart, and other tissues. Spleen is a hematopoietic organ in mouse, and megakaryocytes are sometimes seen trapped in the pulmonary microvasculature. Thus both Northern and in situ hybridization data suggest that PAR3 is most abundantly expressed in megakaryocytes in the mouse.

The pharmacology of hPAR3 activation in Cos cells resembles that of mouse platelet activation. Both responses show subnanomolar $EC_{50}s$ for activation by α-thrombin and are thrombin active site- and fibrinogen-binding exosite-dependent. These observations support the concept that the mouse homolog of PAR3 is a thrombin receptor that mediates thrombin responses in mouse platelets. Whether human PAR3 function in human platelets remains to be determined.

The in situ hybridization studies were performed as follows. Anesthetized adult C57BL/6 mice were perfusion-fixed with 4% paraformaldehyde. Organs to be tested were dissected, trimmed, and immersion-fixed for 4 hours in 4% paraformaldehyde. Processed tissues were embedded in paraffin, and 5 mm sections were cut. Sense or antisense $^{35}$S-riboprobe was transcribed in vitro from mouse PAR2 cDNA subcloned into the EcoR1 site of pBluescript II SK$^-$ (Stratagene, San Diego, Calif.). Hybridization, wash, and development conditions were as reported for mouse PAR1 (Soifer, S. J. et al. (1993) Am. J. Pathol. 144:60–69). To carry out Northern analysis a $^{32}$P-labeled probe for the mouse message was generated by random priming (Prime-It II kit; Stratagene) of PCR-amplified DNA fragments corresponding to mouse cDNA codons representing transmembrane domains 2 to 3. High stringency hybridizations and washes were performed as per the Clontech protocol for Northern analysis.

Northern analysis of human tissues revealed that PAR3 mRNA is widely distributed with signals noted in small intestine, bone marrow, heart, pancreas, lung, liver, adrenal, trachea, lymph node, stomach, and peripheral blood leukocytes. The role of PAR3 in these various human tissues awaits definition; the finding of PAR3 in human bone marrow and leukocytes is consistent with PAR3's playing a role in mediating activation of platelets and other hematopoietic cells by thrombin.

Example 6
Assays for Protease-Activated Receptor 3 Function

Useful receptor fragments or analogs of the invention are those which interact with thrombin and are activated to initiate the cascade of events associated with thrombin:receptor interaction. Such an interaction may be detected by an in vitro functional assay method (e.g., the phosphoinositide hydrolysis assay, $^{45}$Ca efflux assay, or platelet aggregation assay described herein). This method includes, as components, thrombin and a recombinant protease-activated receptor 3 (or a suitable fragment or analog) configured to permit thrombin binding (e.g., those polypeptides described herein). Thrombin may be obtained from Sigma Chemical Co. (St. Louis, Mo.) or similar supplier.

Preferably, the protease-activated receptor 3 component is produced by a cell that naturally presents substantially no receptor on its surface, e.g., by engineering such a cell to contain nucleic acid encoding the receptor component in an appropriate expression system. Suitable cells are, e.g., those discussed above with respect to the production of recombinant receptor, such as Rat 1 cells or COS-7 cells.

Example 7
Screening For Protease-Activated Receptor 3 Activator Antagonists and Agonists Antagonists As discussed above, one aspect of the invention features screening for compounds that inhibit the interaction between thrombin (or other PAR3 activating compound) and the protease-activated receptor 3, thereby preventing or reducing the cascade of events that are mediated by that interaction. The elements of the screen are a PAR3 activator (such as thrombin), a candidate antagonist, and recombinant PAR3 (or a suitable receptor fragment or analog, as outlined above) configured to permit detection of PAR3 activator, antagonist, and PAR3 function. An additional element may be a downstream substrate, such as phosphoinositide, the hydrolysis of which is used to measure thrombin activity (Ishii, K. et al. (1993) supra; and Nanevicz, T. et al. (1996) supra).

Inhibition of thrombin-induced platelet aggregation may also be used as a means of monitoring an antagonist of PAR3 receptor activation. Thrombin is incubated with the candidate inhibitory compound (such as a peptide) for 5 minutes, then the mixture is added to washed platelets and platelet activation is followed as platelet ATP secretion by lumiaggregometry (see, for example, Connolly, A. J. et al. Nature 381:516–519 (1996); and U.S. Pat. No. 5,256,766). Alternately, platelets are incubated with a candidate PAR 3 antagonist for 5 minutes. Thereafter the response to thrombin is measured.

Inclusion of potential antagonists in the screening assay along with thrombin allows for the screening and identification of authentic receptor antagonists as those which decrease thrombin-mediated events, such as platelet aggregation.

Appropriate candidate thrombin antagonists include PAR3 fragments, particularly, fragments of the protein predicted to be extracellular and therefore likely to bind thrombin or the tethered ligand; such fragments would preferably include five or more amino acids. Candidate PAR 3 antagonists include thrombin analogs as well as other peptide and non-peptide compounds and anti-PAR3 antibodies.

Agonists

Another aspect of the invention features screening for compounds that act as PAR3 ligand agonists. Activation of the PAR3 with thrombin or an agonist leads to a cascade of events (such as phosphoinositide hydrolysis, $Ca^{2+}$ efflux, and platelet aggregation), providing a convenient means for measuring thrombin or other agonist activity.

The agonist screening assay of the invention utilizes recombinant cells expressing recombinant PAR3 (or a suitable receptor fragment or analog, as outlined herein) configured to permit detection of PAR3 function. Alternatively, a cell such as a leukocyte, a platelet, or a mesenchymal cell that naturally expresses PAR3 may be used. Other elements of the screen include a detectable downstream substrate of the PAR3 activation, such as radiolabelled phosphoinositide, the hydrolysis of which to a detectable product indicates PAR3 activation by the candidate agonist.

$^{45}$Ca efflux from a cell expressing PAR3 may be used as a means of measuring receptor activation by candidate agonists (Williams, J. A. et al., (1988) PNAS USA 85:4939–4943; Vu, T.-K. H., et al. (1991) Cell 64:1057–1068; and U.S. Pat. No. 5,256,766, which references are herein incorporated by reference in their entirety).

$^{45}$Ca release by oocytes expressing cRNA encoding PAR3 are assessed as follows. Briefly, intracellular calcium pools are labeled by incubating groups of 30 oocytes in 300 µl calcium-free MBSH containing 50 µCi $^{45}CaCl_2$ (10–40 mCi/mg Ca; Amersham) for 4 hours at room temperature. The labeled oocytes are washed, then incubated in MBSH II without antibiotics for 90 minutes. Groups of 5 oocytes are selected and placed in individual wells in a 24-well tissue culture plate (Falcon 3047) containing 0.5 ml/well MBSH II without antibiotics. This medium is removed and replaced with fresh medium every 10 minutes, the harvested medium is analyzed by scintillation counting to determine $^{45}$Ca released by the oocytes during each 10-minute incubation. The 10-minute incubations are continued until a stable baseline of $^{45}$Ca release per unit time is achieved. Two additional 10-minute collections are obtained, then test medium including agonist is added and agonist-induced $^{45}$Ca release determined.

A voltage clamp assay provides an alternative method of monitoring agonist activity. Agonist-induced inward chloride currents are measured in voltage-clamped oocytes expressing thrombin receptor encoding cRNA essentially as previously described (Julius, D. et al. Science (1988) 241:558–563, herein incorporated by reference in its entirety) except that the single electrode voltage-clamp technique is employed.

Platelet aggregation may also be used as a means of monitoring PAR3 receptor activation (see, for example, Connolly, A. J. et al. Nature 381:516–519 (1996). In particular, mouse platelets may utilize only PAR 3 for thrombin signaling. Human platelets may use both PAR 1 and PAR 3. Thus both would be useful in deleting against function at PAR 3.

An agonist useful in the invention is one which imitates the normal thrombin-mediated signal transduction pathway leading, e.g., to an increase in phosphoinositide hydrolysis. Appropriate candidate agonists include thrombin analogs or PAR3 tethered ligand domains or other agents which mimic the action of thrombin or the PAR 3 tethered ligand domain. Agonists would be useful for aiding discovery of antagonists.

Example 8
Anti-Protease-Activated Receptor 3 Antibodies

Protease-activated receptor 3 (or immunogenic receptor fragments or analogs) may be used to raise antibodies useful in the invention. Receptor fragments preferred for the production of antibodies are those fragments deduced or shown experimentally to be extracellular.

Antibodies directed to PAR3 peptides are produced as follows. Peptides corresponding to all or part of the PAR3 protein are produced using a peptide synthesizer by standard techniques. The peptides are coupled to KLH with m-maleimide benzoic acid N-hydroxysuccinimide ester. The KLH-peptide is mixed with Freund's adjuvant and injected into animals, e.g. guinea pigs or goats, to produce polyclonal antibodies. Monoclonal antibodies may be prepared using the PAR3 polypeptides described above and standard hybridoma technology (see, e.g., Kohler et al., Nature (1975) 256:495, 1975; Kohler et al., Eur. J. Immunol. (1976) 6:292; Kohler et al., Eur. J. Immunol. (1976) 6:511; Hammerling et al., in Monoclonal Antibodies and T Cell Hybridomas, Elsevier, N.Y., (1981); and Ausubel et al., supra). Antibodies are purified by peptide antigen affinity chromatography.

Once produced, antibodies are tested for their ability to bind PAR3 by specific binding to the surface of PAR3-transfected cells by Western blot or immunoprecipitation analysis (such as by the methods described in Ausubel et al., supra).

Antibodies which specifically recognize PAR3 are considered to be likely candidates for useful antagonists; such candidates are further tested for their ability to specifically interfere with the interaction between thrombin and PAR3 (using the functional antagonist assays described herein). Antibodies which antagonize thrombin:PAR3 binding or PAR3 function are considered to be useful antagonists in the invention.

Example 9
Therapy

Particularly suitable therapeutics for the treatment of wound healing, thrombosis, atherosclerosis, restenosis, inflammation, and other thrombin-mediated signalling disorders are the agonists and antagonists described above formulated in an appropriate buffer such as physiological saline. Where it is particularly desirable to mimic a receptor fragment conformation at the membrane interface, the fragment may include a sufficient number of adjacent transmembrane residues. In this case, the fragment may be associated with an appropriate lipid fraction (e.g., in lipid vesicles or attached to fragments obtained by disrupting a cell membrane). Alternatively, anti-PAR3 antibodies produced as described above may be used as a therapeutic. Again, the antibodies would be administered in a pharmaceutically-acceptable buffer (e.g., physiological saline). If appropriate, the antibody preparation may be combined with a suitable adjuvant.

Antibodies to PAR 3 are useful antagonists which can be formulated as indicated above. Other therapeutically useful antagonists are peptides derived from PAR3 that bind to and block thrombin and include formulation comprising a pharmaceutically acceptable carrier and one or more of the following:

(1) the isolated sequence LPIKTFRGAPPNSFEEF-PFSALE;

(2) uncleavable thrombin inhibitor LPIKPFRGAPPNS-FEEFPFSALE where the PAR 3 cleavage site P1' is mutated to block cleavage;

(3) uncleavable thrombin inhibitor LPI (hR) TFRGAPPNSFEEFPFSALE where the PAR 3 cleavage site P1 is mutated to block cleavage; hR is beta-homoarginine (the extra methylene group is in the main chain);

(4) uncleavable thrombin inhibitor (dF) PRPFRGAPPNSFEEFPFSALE where the good active site binding sequence dFPR is substituted for LPIK; dF is D-Phenylalanine;

(5) any of (1)–(4) above where all or part of the sequence TFRGAPPNS is replaced with spacer sequences such as GGG;

(6) variations and combinations of (1)–(5) which act as antagonists.

The therapeutic preparation is administered in accordance with the condition to be treated. Ordinarily, it will be administered intravenously, at a dosage, of a duration, and with the appropriate timing to elicit the desired response. Appropriate timing refers to, for example, time relative to wounding, time intervals between therapeutic administrations, and the like, at which administration of therapeutic preparation elicits the desired response. Alternatively, it may be convenient to administer the therapeutic orally, nasally, or topically, e.g., as a liquid or a spray. The dosages are determined to be an amount of the therapeutic agent delivered to an animal that substantially reduces or alleviates disease symptoms. Treatment may be repeated as necessary for substantial reduction or alleviation of disease symptoms.

PAR3 activator agonists can be used for the treatment of bleeding. Antagonists may be useful in controlling the formation of clots that cause heart attack and stroke, mediating inflammation and the proliferative responses to injury in normal wound healing and a variety of diseases including atherosclerosis, restenosis, pulmonary inflammations (ARDS), glomerulosclerosis, etc.

The methods of the invention may be used to screen therapeutic receptor activator agonists and antagonists for their effectiveness in altering thrombin-mediated biological events, such as phosphoinositide hydrolysis or other cell signalling events by the assays described above. Where a non-human mammal is treated or where a therapeutic for a non-human animal is screened, the PAR3 or receptor fragment or analog or the antibody employed is preferably specific for that species.

OTHER EMBODIMENTS

Polypeptides according to the invention include any protease-activated receptors (as described herein). Such receptors may be derived from any source, but are preferably derived from a vertebrate animal, e.g., a human or mouse. These polypeptides are used, e.g., to screen for antagonists which disrupt, or agonists which mimic, a thrombin:receptor interaction.

Polypeptides of the invention also include any analog or fragment of a PAR3 capable of interacting with thrombin. Such analogs and fragments may also be used to screen for PAR3 ligand antagonists or agonists. In addition, that subset of receptor fragments or analogs which bind thrombin and are, preferably, soluble (or insoluble and formulated in a lipid vesicle) may be used as antagonists to reduce the in vivo concentration of endogenous thrombin, either circulating concentration or local concentration. The efficacy of a receptor analog or fragment is dependent upon its ability to interact with thrombin; such an interaction may be readily assayed using PAR3 functional assays (e.g., those described herein).

Specific receptor analogs of interest include full-length or partial receptor proteins including an amino acid sequence which differs only by conservative amino acid substitution, for example, substitution of one amino acid for another of the same class (e.g., valine for leucine, arginine for lysine, etc.) or by one or more non-conservative amino acid substitutions, deletions, or insertions located at positions of the amino acid sequence which do not destroy the receptors' ability to signal thrombin-mediated events (e.g., as assayed above).

Specific receptor fragments of interest include any portion of the PAR3 which is capable of interacting with thrombin, for example, all or part of the extracellular domains predicted from the deduced amino acid sequence. Such fragments may be useful as antagonists (as described above), and are also useful as immunogens for producing antibodies which neutralize the activity of PAR3 in vivo (e.g., by interfering with the interaction between the receptor and thrombin). The sequence of FIG. 5B is most likely to bind thrombin. Modification of the (K38/T39) cleavage site for example, substitution of proline for T39 will render peptides mimicking this site uncleavable. Such peptides will bind thrombin with high affinity.

Extracellular regions of novel protease-activated receptors may be identified by comparison with related proteins of similar structure (e.g., other members of the G-protein-coupled receptor family); useful regions are those exhibiting homology to the extracellular domains of well-characterized members of the family.

Alternatively, from the primary amino acid sequence, the secondary protein structure and, therefore, the extracellular domain regions may be deduced semi-empirically using a hydrophobicity/hydrophilicity calculation such as the Chou-Fasman method (see, e.g., Chou and Fasman, *Ann. Rev. Biochem.* (1978) 47:251). Hydrophilic domains, particularly ones surrounded by hydrophobic stretches (e.g., transmembrane domains) present themselves as strong candidates for extracellular domains. Finally, extracellular domains may be identified experimentally using standard enzymatic digest analysis, e.g., tryptic digest analysis.

Candidate fragments (e.g., any extracellular fragment) are tested for interaction with thrombin by the assays described herein (e.g., the assay described above). Such fragments are also tested for their ability to antagonize the interaction between thrombin and its endogenous receptor, such as PAR3, using the assays described herein. Analogs of useful receptor fragments (as described above) may also be produced and tested for efficacy as screening components or antagonists (using the assays described herein); such analogs are also considered to be useful in the invention.

Identification of the receptor(s) that mediate thrombin signaling provides potential targets for the development of drugs that block thrombin's undesirable actions or mimic its desirable activities. Thrombin receptor antagonists may be used for inhibition of platelet-dependent thrombosis in the setting of unstable angina and myocardial infarction or for blocking thrombin's proinflammatory actions on endothelial cells in the setting of vascular injury. Thrombin receptor agonists may be used to promote hemostasis and fibroblast proliferation at wound sites.

Unmasked tethered ligand domain peptides may provide lead structures for the development of PAR3 agonists or antagonists.

The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

That which is claimed is:

1. Substantially pure DNA having the nucleotide sequence selected from the group consisting of SEQ ID NO:1, or degenerate variants thereof, and encoding the amino acid sequence of SEQ ID NO:3; SEQ ID NO:2, or degenerate variants thereof encoding an amino acid sequence comprising the amino acid sequence of SEQ ID NO:3; SEQ ID NO:4, or degenerate variants thereof encoding the amino acid sequence of SEQ ID NO:6; and SEQ ID NO:5, or degenerate variants thereof encoding an amino acid sequence comprising the amino acid sequence of SEQ ID NO:6.

2. A vector comprising the DNA of claim 1.

3. A cell comprising the vector of claim 2.

4. A substantially pure DNA sequence complementary to a DNA sequence selected from the group consisting of SEQ ID NO:1, or degenerate variants thereof, and encoding the amino acid sequence of SEQ ID NO:3; SEQ ID NO:2, or degenerate variants thereof encoding an amino acid sequence comprising the amino acid sequence of SEQ ID NO:3; SEQ ID NO:4, or degenerate variants thereof encoding the amino acid sequence of SEQ ID NO:6; and SEQ ID NO:5, or degenerate variants thereof encoding an amino acid sequence comprising the amino acid sequence of SEQ ID NO:6.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:

(A) LENGTH: 1224 base pairs
(B) TYPE: nucleic acid
(C) STRANDEDNESS: double
(D) TOPOLOGY: linear (i i) MOLECULE TYPE: cDNA (x i) SEQUENCE DESCRIPTION: SEQ ID NO:1:

| | | | | | | |
|---|---|---|---|---|---|---|
| TGACTTTGTA | TACTTAACAA | CATCCTGTAG | CCGGGTCTCA | GGACATCAAG | ATGAAAATCC | 60 |
| TTATCTTGGT | TGCAGCTGGG | CTGCTGTTTC | TGCCAGTCAC | TGTTTGCCAA | AGTGGCATAA | 120 |
| ATGTTTCAGA | CAACTCAGCA | AAGCCAACCT | TAACTATTAA | GAGTTTTAAT | GGGGTCCCC | 180 |
| AAAATACCTT | TGAAGAATTC | CCACTTTCTG | ACATAGAGGG | CTGGACAGGA | GCCACCACAA | 240 |
| CTATAAAAGC | GGAGTGTCCC | GAGGACAGTA | TTTCAACTCT | CCACGTGAAT | AATGCTACCA | 300 |
| TAGGATACCT | GAGAAGTTCC | TTAAGTACCC | AAGTGATACC | TGCCATCTAT | ATCCTGCTGT | 360 |
| TTGTGGTTGG | TGTACCATCC | AACATCGTGA | CCCTGTGGAA | ACTCTCCTTA | AGGACCAAAT | 420 |
| CCATCAGTCT | GGTCATCTTT | CACACCAACC | TGGCCATCGC | AGATCTCCTT | TTCTGTGTCA | 480 |
| CACTGCCATT | TAAGATCGCC | TACCATCTCA | ATGGCAACAA | CTGGGTATTT | GGCGAGGTCA | 540 |
| TGTGCCGGAT | CACCACGGTC | GTTTCTACG | GCAACATGTA | CTGCGCTATC | CTGATCCTCA | 600 |
| CTTGCATGGG | CATCAACCGC | TACCTGGCCA | CGGCTCACCC | TTTCACATAC | CAGAAGCTGC | 660 |
| CCAAACGCAG | CTTCTCCTTG | CTCATGTGTG | GCATAGTGTG | GGTCATGGTT | TTCTTATACA | 720 |
| TGCTGCCCTT | TGTCATCCTG | AAGCAGGAGT | ACCACCTCGT | CCACTCAGAG | ATCACCACCT | 780 |
| GCCACGATGT | CGTCGACGCG | TGCGAGTCCC | CATCATCCTT | CCGATTCTAC | TACTTCGTCT | 840 |
| CCTTAGCATT | CTTTGGGTTC | CTCATCCCGT | TTGTGATCAT | CATCTTCTGT | TACACGACTC | 900 |
| TCATCCACAA | ACTTAAATCA | AAGGATCGGA | TATGGCTGGG | CTACATCAAG | GCCGTCCTCC | 960 |
| TCATCCTTGT | GATTTTCACA | ATTTGCTTTG | CCCCCACCAA | CATCATACTC | GTAATCCACC | 1020 |
| ATGCCAACTA | CTACTACCAC | AATACCGACA | GCTTGTACTT | TATGTATCTT | ATTGCTCTGT | 1080 |
| GCCTGGGGAG | CCTGAATAGC | TGCCTAGATC | CATTCCTTTA | CTTTGTCATG | TCGAAAGTTG | 1140 |
| TAGATCAGCT | TAATCCTTAG | TCGGCAATGG | CAAGACCACT | TTAGAGACCA | AGGAGAGATA | 1200 |
| TCTGGGAAGA | CATACATGCT | TGGC | | | | 1224 |

(2) INFORMATION FOR SEQ ID NO:2:

(i) SEQUENCE CHARACTERISTICS:
(A) LENGTH: 1124 base pairs
(B) TYPE: nucleic acid
(C) STRANDEDNESS: double
(D) TOPOLOGY: linear (i i) MOLECULE TYPE: Genomic DNA (i x) FEATURE:

(x i) SEQUENCE DESCRIPTION: SEQ ID NO:2:

| | | | | | | |
|---|---|---|---|---|---|---|
| CCATATGCTA | ATATTTCCTT | TCAATTACAG | GCATAAATGT | TTCAGACAAC | TCAGCAAAGC | 60 |
| CAACCTTAAC | TATTAAGAGT | TTTAATGGGG | GTCCCCAAAA | TACCTTTGAA | GAATTCNNNN | 120 |
| NNNTACAACT | CTCCATGTGA | ATAATGCTAC | CATGGGATAC | CTGAGAAGTT | CCTTAAGTAC | 180 |
| CAAAGTGATA | CCTGCCATCT | ACATCCTGGT | GTTTGTGATT | GGTGTACCAG | CGAACATCGT | 240 |
| GACCCTGTGG | AAACTCTCCT | CAAGGACCAA | ATCCATCTGT | CTGGTCATCT | TTCACACCAA | 300 |
| CCTGGCCATC | GCGGATCTCC | TTTTCTGTGT | CACGCTGCCG | TTTAAGATCN | NCCTACCATC | 360 |
| TCAATGGCAA | CAACTGGGTA | TTTGGCGAGG | TCATGTGCCG | GATCACCACG | GTCGTTTTCT | 420 |

-continued

| | | | | | |
|---|---|---|---|---|---|
| ACGGCAACAT | GTACTGCGCT | ANNNTCCTGA | TCCTCACCTG | CATGGGCATC | AACCGCTACC | 480 |
| TGGCCACGGC | TCACCCTTTC | ACATACCAGA | AGCTGCCCAA | ACGCAGCTTC | TCCATGCTCA | 540 |
| TGTGTGGCAT | GGTGTGGGTC | ATGGTTTTCT | TATACATGCT | GCCCTTTGTC | ATCCNNNAAG | 600 |
| CAGGAGTACC | ACCTCGTCCA | CTCCGAGATC | ACCACCTGCC | ACGATGTCGT | CGACGCGTGC | 660 |
| GANTCCCCAT | CATCCTTCCG | ATTCTACTAC | TTCGTCTCCT | TAGCATTCTT | TGGGTTCCTC | 720 |
| ATCCCGTTTG | TGATCATCAT | CTTCTGTTAC | ACGACTCTCA | TCCACAAACT | TAAATCAAAA | 780 |
| GATCNGATAT | GGCTGGGCTA | CATCAAGGCC | GTCCTCCTCA | TCCTTGTGAA | TTTCACCATC | 840 |
| TGCTTCCCCC | CCACCAAGNN | NNNNGATATC | TGGGAAGACG | TACATGCTTG | GCTGACTTGT | 900 |
| GCATGGCACC | ATCAGCTCAA | TTTTTAATTT | TTTAATTTTA | ATTTAATTTA | ATTTTATGTT | 960 |
| TTTGAGACAG | AGCCTCACTG | TGTAGTCCTG | GCTGGCCTGG | CTGGTTCTCT | ATTTAGACCA | 1020 |
| GGTTAGCCTT | GAACTCACAG | AGATCTGCCT | GCTTCTGCCT | CCCAAGTGCT | GGGTTCAACC | 1080 |
| AGGTCTGGCA | AGCGCTCCAT | TTTTCAGCTC | CTCTGCAACA | GTGC | | 1124 |

( 2 ) INFORMATION FOR SEQ ID NO:3:

( i ) SEQUENCE CHARACTERISTICS:
  ( A ) LENGTH: 407 amino acids
  ( B ) TYPE: amino acid
  ( C ) STRANDEDNESS: single
  ( D ) TOPOLOGY: linear ( i i ) MOLECULE TYPE: protein ( i x ) FEATURE:

( x i ) SEQUENCE DESCRIPTION: SEQ ID NO:3:

```
Thr Leu Tyr Thr Xaa Gln His Pro Val Ala Gly Ser Gln Asp Ile Lys
 1               5                  10                  15

Met Lys Ile Leu Ile Leu Val Ala Ala Gly Leu Leu Phe Leu Pro Val
                20                  25                  30

Thr Val Cys Gln Ser Gly Ile Asn Val Ser Asp Asn Ser Ala Lys Pro
                35                  40                  45

Thr Leu Thr Ile Lys Ser Phe Asn Gly Gly Pro Gln Asn Thr Phe Glu
 50                  55                  60

Glu Phe Pro Leu Ser Asp Ile Glu Gly Trp Thr Gly Ala Thr Thr Thr
 65                  70                  75                  80

Ile Lys Ala Glu Cys Pro Glu Asp Ser Ile Ser Thr Leu His Val Asn
                85                  90                  95

Asn Ala Thr Ile Gly Tyr Leu Arg Ser Ser Leu Ser Thr Gln Val Ile
                100                 105                 110

Pro Ala Ile Tyr Ile Leu Leu Phe Val Val Gly Val Pro Ser Asn Ile
                115                 120                 125

Val Thr Leu Trp Lys Leu Ser Leu Arg Thr Lys Ser Ile Ser Leu Val
 130                 135                 140

Ile Phe His Thr Asn Leu Ala Ile Ala Asp Leu Leu Phe Cys Val Thr
 145                 150                 155                 160

Leu Pro Phe Lys Ile Ala Tyr His Leu Asn Gly Asn Asn Trp Val Phe
                165                 170                 175

Gly Glu Val Met Cys Arg Ile Thr Thr Val Val Phe Tyr Gly Asn Met
                180                 185                 190

Tyr Cys Ala Ile Leu Ile Leu Thr Cys Met Gly Ile Asn Arg Tyr Leu
                195                 200                 205

Ala Thr Ala His Pro Phe Thr Tyr Gln Lys Leu Pro Lys Arg Ser Phe
 210                 215                 220
```

```
Ser  Leu  Leu  Met  Cys  Gly  Ile  Val  Trp  Val  Met  Val  Phe  Leu  Tyr  Met
225                 230                      235                      240

Leu  Pro  Phe  Val  Ile  Leu  Lys  Gln  Glu  Tyr  His  Leu  Val  His  Ser  Glu
                    245                      250                      255

Ile  Thr  Thr  Cys  His  Asp  Val  Val  Asp  Ala  Cys  Glu  Ser  Pro  Ser  Ser
               260                      265                      270

Phe  Arg  Phe  Tyr  Tyr  Phe  Val  Ser  Leu  Ala  Phe  Phe  Gly  Phe  Leu  Ile
          275                      280                      285

Pro  Phe  Val  Ile  Ile  Ile  Phe  Cys  Tyr  Thr  Thr  Leu  Ile  His  Lys  Leu
     290                      295                      300

Lys  Ser  Lys  Asp  Arg  Ile  Trp  Leu  Gly  Tyr  Ile  Lys  Ala  Val  Leu  Leu
305                 310                      315                      320

Ile  Leu  Val  Ile  Phe  Thr  Ile  Cys  Phe  Ala  Pro  Thr  Asn  Ile  Ile  Leu
               325                      330                      335

Val  Ile  His  His  Ala  Asn  Tyr  Tyr  Tyr  His  Asn  Thr  Asp  Ser  Leu  Tyr
               340                      345                      350

Phe  Met  Tyr  Leu  Ile  Ala  Leu  Cys  Leu  Gly  Ser  Leu  Asn  Ser  Cys  Leu
               355                      360                      365

Asp  Pro  Phe  Leu  Tyr  Phe  Val  Met  Ser  Lys  Val  Val  Asp  Gln  Leu  Asn
     370                      375                      380

Pro  Xaa  Ser  Ala  Met  Ala  Arg  Pro  Leu  Xaa  Arg  Pro  Arg  Arg  Asp  Ile
385                 390                      395                      400

Trp  Glu  Asp  Ile  His  Ala  Trp
                    405
```

( 2 ) INFORMATION FOR SEQ ID NO:4:

( i ) SEQUENCE CHARACTERISTICS:
( A ) LENGTH: 1224 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:4:

```
TGCTCCATGA  TTTTACAGAT  TTCATAACGT  TTAAGAGACG  GGACTCAGGT  CATCAAAATG   60
AAAGCCCTCA  TCTTTGCAGC  TGCTGGCCTC  CTGCTTCTGT  TGCCCACTTT  TTGTCAGAGT  120
GGCATGGAAA  ATGATACAAA  CAACTTGGCA  AAGCCAACCT  TACCCATTAA  GACCTTTCGT  180
GGAGCTCCCC  CAAATTCTTT  TGAAGAGTTC  CCCTTTTCTG  CCTTGGAAGG  CTGGACAGGA  240
GCCACGATTA  CTGTAAAAAT  TAAGTGCCCT  GAAGAAAGTG  CTTCACATCT  CCATGTGAAA  300
AATGCTACCA  TGGGGTACCT  GACCAGCTCC  TTAAGTACTA  AACTGATACC  TGCCATCTAC  360
CTCCTGGTGT  TTGTAGTTGG  TGTCCCGGCC  AATGCTGTGA  CCCTGTGGAT  GCTTTTCTTC  420
AGGACCAGAT  CCATCTGTAC  CACTGTATTC  TACACCAACC  TGGCCATTGC  AGATTTTCTT  480
TTTTGTGTTA  CATTGCCCTT  TAAGATAGCT  TATCATCTCA  ATGGGACAAC  TGGGTATTT  540
GGAGAGGTCC  TGTGCCGGGC  CACCACAGTC  ATCTTCTATG  CAACATGTA  CTGCTCCATT  600
CTGCTCCTTG  CCTGCATCAG  CATCAACCGC  TACCTGGCCA  TCGTCCATCC  TTTCACCTAC  660
CGGGGCCTGC  CCAAGCACAC  CTATGCCTTG  GTAACATGTG  ACTGGTGTG  GGCAACAGTT  720
TTCTTATATA  TGCTGCCATT  TTTCATACTG  AAGCAGGAAT  ATTATCTTGT  TCAGCCAGAC  780
ATCACCACCT  GCCATGATGT  TCACAACACT  TGCGAGTCCT  CATCTCCCTT  CCAACTCTAT  840
TACTTCATCT  CCTTGGCATT  CTTTGGATTC  TTAATTCCAT  TTGTGCTTAT  CATCTACTGC  900
```

-continued

```
TATGCAGCCA TCATCCGGAC ACTTAATGCA TACGATCATA GATGGTTGTG GTATGTTAAG      960
GCGAGTCTCC TCATCCTTGT GATTTTTACC ATTTGCTTTG CTCCAAGCAA TATTATTCTT     1020
ATTATTCACC ATGCTAACTA CTACTACAAC AACACTGATG CTTATATTT TATATATCTC     1080
ATAGCTTTGT GCCTGGGTAG TCTTAATAGT TGCTTAGATC CATTCCTTTA TTTTCTCATG    1140
TCAAAAACCA GAAATCACTC CACTGCTTAC CTTACAAAAT AGTGAAATGA TCTTAGAGAA    1200
CAAGGACAGC CATCACAGAG AACG                                           1224
```

(2) INFORMATION FOR SEQ ID NO:5:

(i) SEQUENCE CHARACTERISTICS:
        (A) LENGTH: 1102 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:5:

```
ACAGGCATGG AAAATGATAC AAACAACTTG GCAAAGCCAA CCTTACCCAT TAAGACCTTT       60
CGTGGAGCTC CCCCAAATTC TTTTGAAGAG TTCCCCTTTT CTGCCTTGGA AGGCTGGACA      120
GGAGCCACGA TTACTGTAAA AATTAAGTGC CCTGAAGAAA GTGCTTCACA TCTCCATGTG      180
AAAAATGCTA CCATGGGGTA CCTGACCAGC TCCTTAAGTA CTAAACTGAT ACCTGCCATC      240
TACCTCCTGG TGTTTGTAGT TGGTGTCCCG GCCAATGCTG TGACCCTGTG GATGCTTTTC      300
TTCAGGACCA GATCCATCTG TACCACTGTA TTCTACACCA ACCTGGCCAT TGCAGATTTT      360
CTTTTTTGTG TTACATTGCC CTTTAAGATA GCTTATCATC TCAATGGGAA CAACTGGGTA      420
TTTGGAGAGG TCCTGTGCCG GGCCACCACA GTCATCTTCT ATGGCAACAT GTACTGCTCC      480
ATTCTGCTCC TTGCCTGCAT CAGCATCAAC CGCTACCTGG CCATCGTCCA TCCTTTCACC      540
TACCGGGGCC TGCCCAAGCA CACCTATGCC TTGGTAACAT GTGGACTGGT GTGGGCAACA      600
GTTTTCTTAT ATATGCTGCC ATTTTTCATA CTGAAGCAGG AATATTATCT TGTTCAGCCA      660
GACATCACCA CCTGCCATGA TGTTCACAAC ACTTGCGAGT CCTCATCTCC CTTCCAACTC      720
TATTACTTCA TCTCCTTGGC ATTCTTTGGA TTCTTAATTC CATTTGTGCT TATCATCTAC      780
TGCTATGCAG CCATCATCCG GACACTTAAT GCATACGATC ATAGATGGTT GTGGTATGTT      840
AAGGCGAGTC TCCTCATCCT TGTGATTTTT ACCATTTGCT TTGCTCCAAG CAATATTATT      900
CTTATTATTC ACCATGCTAA CTACTACTAC AACAACACTG ATGGCTTATA TTTTATATAT      960
CTCATAGCTT TGTGCCTGGG TAGTCTTAAT AGTTGCTTAG ATCCATTCCT TTATTTTCTC     1020
ATGTCAAAAA CCAGAAATCA CTCCACTGCT TACCTTACAA AATAGTGAAA TGATCTTAGA     1080
GAACAAGGAC AGCCATCACA GA                                              1102
```

(2) INFORMATION FOR SEQ ID NO:6:

(i) SEQUENCE CHARACTERISTICS:
        (A) LENGTH: 408 amino acids
        (B) TYPE: amino acid
        (C) STRANDEDNESS: single
        (D) TOPOLOGY: linear (ix) FEATURE:

(xi) SEQUENCE DESCRIPTION: SEQ ID NO:6:

```
Cys Ser Met Ile Leu Gln Ile Ser Xaa Arg Leu Arg Asp Gly Thr Gln
 1               5                  10                  15

Val Ile Lys Met Lys Ala Leu Ile Phe Ala Ala Ala Gly Leu Leu Leu
```

|     |     |     |     | 20  |     |     |     |     | 25  |     |     |     |     | 30  |     |
| --- | --- | --- | --- | --- | --- | --- | --- | --- | --- | --- | --- | --- | --- | --- | --- |
| Leu | Leu | Pro<br>35 | Thr | Phe | Cys | Gln | Ser<br>40 | Gly | Met | Glu | Asn | Asp<br>45 | Thr | Asn | Asn |
| Leu | Ala | Lys<br>50 | Pro | Thr | Leu | Pro<br>55 | Ile | Lys | Thr | Phe | Arg<br>60 | Gly | Ala | Pro | Pro |
| Asn<br>65 | Ser | Phe | Glu | Glu | Phe<br>70 | Pro | Phe | Ser | Ala | Leu<br>75 | Glu | Gly | Trp | Thr | Gly<br>80 |
| Ala | Thr | Ile | Thr | Val<br>85 | Lys | Ile | Lys | Cys | Pro<br>90 | Glu | Glu | Ser | Ala | Ser<br>95 | His |
| Leu | His | Val | Lys<br>100 | Asn | Ala | Thr | Met | Gly<br>105 | Tyr | Leu | Thr | Ser | Ser<br>110 | Leu | Ser |
| Thr | Lys | Leu | Ile<br>115 | Pro | Ala | Ile | Tyr<br>120 | Leu | Leu | Val | Phe | Val<br>125 | Val | Gly | Val |
| Pro | Ala | Asn<br>130 | Ala | Val | Thr | Leu<br>135 | Trp | Met | Leu | Phe | Phe<br>140 | Arg | Thr | Arg | Ser |
| Ile | Cys<br>145 | Thr | Thr | Val | Phe<br>150 | Tyr | Thr | Asn | Leu | Ala<br>155 | Ile | Ala | Asp | Phe | Leu<br>160 |
| Phe | Cys | Val | Thr | Leu<br>165 | Pro | Phe | Lys | Ile | Ala<br>170 | Tyr | His | Leu | Asn | Gly<br>175 | Asn |
| Asn | Trp | Val | Phe<br>180 | Gly | Glu | Val | Leu | Cys<br>185 | Arg | Ala | Thr | Thr | Val<br>190 | Ile | Phe |
| Tyr | Gly | Asn<br>195 | Met | Tyr | Cys | Ser | Ile<br>200 | Leu | Leu | Leu | Ala | Cys<br>205 | Ile | Ser | Ile |
| Asn | Arg<br>210 | Tyr | Leu | Ala | Ile | Val<br>215 | His | Pro | Phe | Thr | Tyr<br>220 | Arg | Gly | Leu | Pro |
| Lys<br>225 | His | Thr | Tyr | Ala | Leu<br>230 | Val | Thr | Cys | Gly | Leu<br>235 | Val | Trp | Ala | Thr | Val<br>240 |
| Phe | Leu | Tyr | Met | Leu<br>245 | Pro | Phe | Phe | Ile | Leu<br>250 | Lys | Gln | Glu | Tyr | Tyr<br>255 | Leu |
| Val | Gln | Pro | Asp<br>260 | Ile | Thr | Thr | Cys | His<br>265 | Asp | Val | His | Asn | Thr<br>270 | Cys | Glu |
| Ser | Ser | Ser<br>275 | Pro | Phe | Gln | Leu | Tyr<br>280 | Tyr | Phe | Ile | Ser | Leu<br>285 | Ala | Phe | Phe |
| Gly | Phe<br>290 | Leu | Ile | Pro | Phe<br>295 | Val | Leu | Ile | Ile | Tyr<br>300 | Cys | Tyr | Ala | Ala | Ile |
| Ile<br>305 | Arg | Thr | Leu | Asn | Ala<br>310 | Tyr | Asp | His | Arg | Leu<br>315 | Trp | Tyr | Val | Lys<br>320 |     |
| Ala | Ser | Leu | Leu | Ile<br>325 | Leu | Val | Ile | Phe | Thr<br>330 | Ile | Cys | Phe | Ala | Pro<br>335 | Ser |
| Asn | Ile | Ile | Leu<br>340 | Ile | Ile | His | His | Ala<br>345 | Asn | Tyr | Tyr | Tyr | Asn<br>350 | Asn | Thr |
| Asp | Gly | Leu<br>355 | Tyr | Phe | Ile | Tyr | Leu<br>360 | Ile | Ala | Leu | Cys | Leu<br>365 | Gly | Ser | Leu |
| Asn | Ser<br>370 | Cys | Leu | Asp | Pro | Phe<br>375 | Leu | Tyr | Phe | Leu | Met<br>380 | Ser | Lys | Thr | Arg |
| Asn | His | Ser | Thr | Ala | Tyr | Leu | Thr | Lys | Xaa | Xaa | Asn | Asp | Leu | Arg | Glu |
| 385 |     |     |     |     | 390 |     |     |     | 395 |     |     |     |     |     | 400 |
| Gln | Gly | Gln | Pro | Ser<br>405 | Gln | Arg | Thr |     |     |     |     |     |     |     |     |

( 2 ) INFORMATION FOR SEQ ID NO:7:

( i ) SEQUENCE CHARACTERISTICS:
        ( A ) LENGTH: 425 amino acids
        ( B ) TYPE: amino acid (C) STRANDEDNESS: single
(D) TOPOLOGY: linear (ii) MOLECULE TYPE: protein (xi) SEQUENCE DESCRIPTION: SEQ ID NO:7:

```
Met Gly Pro Arg Arg Leu Leu Leu Val Ala Ala Cys Phe Ser Leu Cys
 1               5                  10                  15

Gly Pro Leu Leu Ser Ala Arg Thr Arg Ala Arg Arg Pro Glu Ser Lys
                20                  25                  30

Ala Thr Asn Ala Thr Leu Asp Pro Arg Ser Phe Leu Leu Arg Asn Pro
            35                  40                  45

Asn Asp Lys Tyr Glu Pro Phe Trp Glu Asp Glu Lys Asn Glu Ser
    50                  55                  60

Gly Leu Thr Glu Tyr Arg Leu Val Ser Ile Asn Lys Ser Ser Pro Leu
 65                 70                  75                  80

Gln Lys Gln Leu Pro Ala Phe Ile Ser Glu Asp Ala Ser Gly Tyr Leu
                85                  90                  95

Thr Ser Ser Trp Leu Thr Leu Phe Val Pro Ser Val Tyr Thr Gly Val
            100                 105                 110

Phe Val Val Ser Leu Pro Leu Asn Ile Met Ala Ile Val Val Phe Ile
            115                 120                 125

Leu Lys Met Lys Val Lys Lys Pro Ala Val Val Tyr Met Leu His Leu
    130                 135                 140

Ala Thr Ala Asp Val Leu Phe Val Ser Val Leu Pro Phe Lys Ile Ser
145                 150                 155                 160

Tyr Tyr Phe Ser Gly Ser Asp Trp Gln Phe Gly Ser Glu Leu Cys Arg
                165                 170                 175

Phe Val Thr Ala Ala Phe Tyr Cys Asn Met Tyr Ala Ser Ile Leu Leu
            180                 185                 190

Met Thr Val Ile Ser Ile Asp Arg Phe Leu Ala Val Val Tyr Pro Met
            195                 200                 205

Gln Ser Leu Ser Trp Arg Thr Leu Gly Arg Ala Ser Phe Thr Cys Leu
    210                 215                 220

Ala Ile Trp Ala Leu Ala Ile Ala Gly Val Val Pro Leu Val Leu Lys
225                 230                 235                 240

Glu Gln Thr Ile Gln Val Pro Gly Leu Asn Ile Thr Thr Cys His Asp
                245                 250                 255

Val Leu Asn Glu Thr Leu Leu Glu Gly Tyr Tyr Ala Tyr Tyr Phe Ser
            260                 265                 270

Ala Phe Ser Ala Val Phe Phe Phe Val Pro Leu Ile Ile Ser Thr Val
            275                 280                 285

Cys Tyr Val Ser Ile Ile Arg Cys Leu Ser Ser Ser Ala Val Ala Asn
    290                 295                 300

Arg Ser Lys Lys Ser Arg Ala Leu Phe Leu Ser Ala Ala Val Phe Cys
305                 310                 315                 320

Ile Phe Ile Ile Cys Phe Gly Pro Thr Asn Val Leu Leu Ile Ala His
                325                 330                 335

Tyr Ser Phe Leu Ser His Thr Ser Thr Thr Glu Ala Ala Tyr Phe Ala
            340                 345                 350

Tyr Leu Leu Cys Val Cys Val Ser Ile Ser Ser Cys Ile Asp Pro
            355                 360                 365

Leu Ile Tyr Tyr Tyr Ala Ser Ser Glu Cys Gln Arg Tyr Val Tyr Ser
    370                 375                 380

Ile Leu Cys Cys Lys Glu Ser Ser Asp Pro Ser Ser Tyr Asn Ser Ser
```

|  |  | 385 |  |  |  |  | 390 |  |  |  |  | 395 |  |  |  |  | 400 |
| --- |

Gly Gln Leu Met Ala Ser Lys Met Asp Thr Cys Ser Ser Asn Leu Asn
                405                     410                     415

Asn Ser Ile Tyr Lys Lys Leu Leu Thr
            420                 425

(2) INFORMATION FOR SEQ ID NO:8:

(i) SEQUENCE CHARACTERISTICS:
        (A) LENGTH: 394 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Met Arg Ser Pro Ser Ala Ala Trp Leu Leu Gly Ala Ala Ile Leu Leu
 1               5                  10                      15

Ala Ala Ser Leu Ser Cys Ser Gly Thr Ile Gln Gly Thr Asn Arg Ser
            20                  25                  30

Ser Lys Gly Arg Ser Leu Ile Gly Lys Val Asp Gly Thr Ser His Val
        35                  40                  45

Thr Gly Lys Gly Val Thr Val Glu Thr Val Phe Ser Val Asp Glu Phe
    50                  55                  60

Ser Ala Ser Val Leu Thr Gly Lys Leu Thr Thr Val Phe Leu Pro Ile
65                  70                  75                  80

Val Tyr Thr Ile Val Phe Val Val Gly Leu Pro Ser Asn Gly Met Ala
                85                  90                  95

Leu Trp Val Phe Leu Phe Arg Thr Lys Lys His Pro Ala Val Ile
                100                 105                 110

Tyr Met Ala Asn Leu Ala Leu Ala Asp Leu Leu Ser Val Ile Trp Phe
            115                 120                 125

Pro Leu Lys Ile Ala Tyr His Ile His Gly Asn Asn Trp Ile Tyr Gly
        130                 135                 140

Glu Ala Leu Cys Asn Val Leu Ile Gly Phe Phe Tyr Gly Asn Met Tyr
145                 150                 155                 160

Cys Ser Ile Leu Phe Met Thr Cys Leu Ser Val Gln Arg Tyr Trp Val
                165                 170                 175

Ile Val Asn Pro Met Gly His Ser Arg Lys Lys Ala Asn Ile Ala Ile
            180                 185                 190

Gly Ile Ser Leu Ala Ile Trp Leu Leu Ile Leu Leu Val Thr Ile Pro
        195                 200                 205

Leu Tyr Val Val Lys Gln Thr Ile Phe Ile Pro Ala Leu Asn Ile Thr
    210                 215                 220

Thr Cys His Asp Val Leu Pro Glu Gln Leu Leu Val Gly Asp Pro Phe
225                 230                 235                 240

Leu Ser Leu Ala Ile Gly Val Phe Leu Phe Pro Ala Phe Leu Thr Ala
                245                 250                 255

Ser Ala Tyr Val Leu Met Ile Arg Met Leu Arg Ser Ser Ala Met Asp
            260                 265                 270

Glu Asn Ser Glu Lys Lys Arg Lys Arg Ala Ile Lys Leu Ile Val Thr
        275                 280                 285

Val Leu Ala Met Tyr Leu Ile Cys Phe Thr Pro Ser Asn Leu Leu Leu
    290                 295                 300

Val Val His Tyr Phe Leu Ile Lys Ser Gln Gly Gln Ser His Val Tyr
305                 310                 315                 320

```
Ala  Leu  Tyr  Ile  Val  Ala  Leu  Cys  Leu  Ser  Thr  Leu  Asn  Ser  Cys  Ile
               325                      330                          335

Asp  Pro  Phe  Val  Tyr  Tyr  Phe  Val  Ser  His  Asp  Phe  Arg  Asp  His  Ala
               340                      345                          350

Lys  Asn  Ala  Leu  Leu  Cys  Arg  Ser  Val  Arg  Thr  Val  Lys  Gln  Met  Gln
          355                      360                     365

Val  Ser  Leu  Thr  Ser  Lys  Lys  His  Ser  Arg  Lys  Ser  Ser  Ser  Tyr  Ser
     370                      375                     380

Ser  Ser  Ser  Thr  Thr  Val  Lys  Thr  Ser  Tyr
385                      390
```

(2) INFORMATION FOR SEQ ID NO:9:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Asp  Phe  Glu  Glu  Ile  Pro  Glu  Glu  Tyr  Leu  Gln
1                   5                        10
```

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Other
        (B) LOCATION: 1...29
        (D) OTHER INFORMATION: N=Inosine at residues 3, 12, 18, 21,
            and 24
        (A) NAME/KEY: Other
        (B) LOCATION: 22...27
        (D) OTHER INFORMATION: N=A or C or G or T at residues 22 and
            27

(xi) SEQUENCE DESCRIPTION: SEQ ID NO:10:

```
GTNTACATGC  TNMACYTNGC  NNTNGCNGA                                          29
```

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Other
        (B) LOCATION: 6...21
        (D) OTHER INFORMATION: N=Inosine at residues 6, 9, 12, 15, and
            21
        (A) NAME/KEY: Other
        (B) LOCATION: 24
        (D) OTHER INFORMATION: N=A or C or G or T at residue 24

(xi) SEQUENCE DESCRIPTION: SEQ ID NO:11:

```
GGATANACNA  CNGCNADRWA  NCKNTC                                             26
```

( 2 ) INFORMATION FOR SEQ ID NO:12:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( x i ) SEQUENCE DESCRIPTION: SEQ ID NO:12:

Asp Tyr Lys Asp Asp Asp
 1               5

( 2 ) INFORMATION FOR SEQ ID NO:13:

( i ) SEQUENCE CHARACTERISTICS:
( A ) LENGTH: 39 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:13:

Met Asp Ser Lys Gly Ser Ser Gln Lys Gly Ser Arg Leu Leu Leu Leu
 1               5                  10                  15

Leu Val Val Ser Asn Leu Leu Leu Cys Gln Gly Val Val Ser Asp Tyr
            20                  25                  30

Lys Asp Asp Asp Asp Val Glu
            35

( 2 ) INFORMATION FOR SEQ ID NO:14:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:14:

Phe Glu Glu Phe Pro
 1               5

( 2 ) INFORMATION FOR SEQ ID NO:15:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( x i ) SEQUENCE DESCRIPTION: SEQ ID NO:15:

Leu Thr Pro Lys
 1

( 2 ) INFORMATION FOR SEQ ID NO:16:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:16:

```
Thr  Phe  Arg  Gly  Ala  Pro
 1                  5
```

( 2 ) INFORMATION FOR SEQ ID NO:17:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:17:

```
Thr  Phe  Arg  Gly  Ala  Pro  Pro  Asn  Ser
 1                  5
```

( 2 ) INFORMATION FOR SEQ ID NO:18:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:18:

```
Leu  Pro  Ile  Lys  Thr  Phe  Arg  Gly  Ala  Pro  Pro  Asn  Ser  Phe  Glu  Glu
 1                  5                            10                           15
Phe  Pro  Phe  Ser  Ala  Leu  Glu
                    20
```

( 2 ) INFORMATION FOR SEQ ID NO:19:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:19:

```
Leu  Pro  Ile  Lys  Pro  Phe  Arg  Gly  Ala  Pro  Pro  Asn  Ser  Phe  Glu  Glu
 1                  5                            10                           15
Phe  Pro  Phe  Ser  Ala  Leu  Glu
                    20
```

( 2 ) INFORMATION FOR SEQ ID NO:20:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i x ) FEATURE:

( x i ) SEQUENCE DESCRIPTION: SEQ ID NO:20:

```
Leu  Pro  Ile  Xaa  Thr  Pro  Phe  Arg  Gly  Ala  Pro  Pro  Asn  Ser  Phe  Glu
 1                  5                            10                           15
Glu  Phe  Pro  Phe  Ser  Ala  Leu  Glu
                    20
```

( 2 ) INFORMATION FOR SEQ ID NO:21:

( i ) SEQUENCE CHARACTERISTICS:
        ( A ) LENGTH: 22 amino acids
        ( B ) TYPE: amino acid (C) STRANDEDNESS: single
        (D) TOPOLOGY: linear (ix) FEATURE:

(xi) SEQUENCE DESCRIPTION: SEQ ID NO:21:

Xaa Pro Arg Pro Phe Arg Gly Ala Pro Pro Asn Ser Phe Glu Glu Phe
1               5                   10                  15

Pro Phe Ser Ala Leu Glu
            20

(2) INFORMATION FOR SEQ ID NO:22:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

Leu Pro Ile Lys
1

(2) INFORMATION FOR SEQ ID NO:23:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:23:

Thr Phe Arg Gly Ala Pro Pro Asn Ser
1               5